(12) United States Patent
Jones et al.

(10) Patent No.: US 8,876,687 B2
(45) Date of Patent: Nov. 4, 2014

(54) SURGICAL RETRACTOR AND RETRACTOR ASSEMBLY

(75) Inventors: Robert J. Jones, Austin, TX (US); Kameron S. Ely, Cedar Park, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 1679 days.

(21) Appl. No.: 11/683,340

(22) Filed: Mar. 7, 2007

(65) Prior Publication Data
US 2007/0238932 A1    Oct. 11, 2007

Related U.S. Application Data

(60) Provisional application No. 60/780,929, filed on Mar. 8, 2006.

(51) Int. Cl.
*A61B 1/32* (2006.01)
*A61B 17/02* (2006.01)

(52) U.S. Cl.
CPC ............ *A61B 17/0293* (2013.01); *A61B 17/02* (2013.01)
USPC ........................................... 600/21; 600/219

(58) Field of Classification Search
CPC .................................................. A16B 17/0293
USPC .......... 600/213–215, 219, 222, 224–225, 233
See application file for complete search history.

(56) References Cited

U.S. PATENT DOCUMENTS

| | | | |
|---|---|---|---|
| 3,384,078 A | 5/1968 | Gauthier | |
| 3,965,890 A | 6/1976 | Gauthier | |
| 4,616,635 A * | 10/1986 | Caspar et al. | 600/215 |
| 4,747,394 A | 5/1988 | Watanabe | |
| 4,817,587 A | 4/1989 | Janese | |
| 5,035,232 A | 7/1991 | Lutze et al. | |
| 5,125,396 A | 6/1992 | Ray | |
| 5,284,129 A | 2/1994 | Agbodoe et al. | |
| 5,299,563 A | 4/1994 | Seton | |
| 5,375,481 A | 12/1994 | Cabrera et al. | |
| 5,512,038 A | 4/1996 | O'Neal et al. | |
| 5,520,608 A | 5/1996 | Cabrera et al. | |
| 5,667,481 A * | 9/1997 | Villalta et al. | 600/224 |
| 5,688,223 A * | 11/1997 | Rosendahl | 600/215 |

(Continued)

FOREIGN PATENT DOCUMENTS

| | | |
|---|---|---|
| DE | 3834358 | 4/1990 |
| EP | 0428567 | 5/1996 |

(Continued)

*Primary Examiner* — Matthew Lawson
(74) *Attorney, Agent, or Firm* — Seager, Tufte & Wickhem, LLC

(57) ABSTRACT

Retractor for insertion in an incision of a patient includes a frame defining a central opening and a reference plane, and at least one blade disposed within the central opening. The blade operatively coupled to the frame by a support structure for movement in a first direction generally laterally with the reference plane between an unretracted position and a retracted position, a second direction at an angle extending through and relative to the reference plane for adjustment of the blade depth, and a third direction rotationally relative to the reference plane. Additionally, the frame includes a track in mating relationship with the support structure for sliding movement therebetween in a defined relationship relative to the reference plane. Retractor assembly includes the retractor as previously described, in combination with an adjustment tool or an insertion tool.

14 Claims, 19 Drawing Sheets

(56) References Cited

U.S. PATENT DOCUMENTS

| | | | |
|---|---|---|---|
| 5,865,731 A | 2/1999 | Lenox et al. | |
| 5,882,298 A | 3/1999 | Sharratt | |
| 5,888,197 A | 3/1999 | Mulac et al. | |
| 5,893,831 A * | 4/1999 | Koros et al. | 600/232 |
| 5,902,233 A | 5/1999 | Farley et al. | |
| 5,928,139 A | 7/1999 | Koros et al. | |
| 5,944,658 A | 8/1999 | Koros et al. | |
| 5,967,973 A | 10/1999 | Sherts et al. | |
| 5,984,865 A | 11/1999 | Farley et al. | |
| 6,030,340 A | 2/2000 | Maffei et al. | |
| 6,042,542 A | 3/2000 | Koros et al. | |
| 6,083,154 A | 7/2000 | Liu et al. | |
| 6,102,854 A * | 8/2000 | Cartier et al. | 600/228 |
| 6,139,493 A | 10/2000 | Koros et al. | |
| 6,190,312 B1 | 2/2001 | Fowler | |
| 6,241,659 B1 | 6/2001 | Bookwalter et al. | |
| 6,254,532 B1 | 7/2001 | Paolitto et al. | |
| 6,306,085 B1 | 10/2001 | Farascioni | |
| 6,361,488 B1 | 3/2002 | Davison et al. | |
| 6,416,470 B2 | 7/2002 | Paolitto et al. | |
| 6,431,025 B1 * | 8/2002 | Koros et al. | 74/577 M |
| 6,464,634 B1 | 10/2002 | Fraser | |
| 6,468,207 B1 | 10/2002 | Fowler | |
| 6,520,967 B1 | 2/2003 | Cauthen | |
| 6,530,883 B2 | 3/2003 | Bookwalter et al. | |
| 6,569,168 B2 | 5/2003 | Lin | |
| 6,572,540 B2 | 6/2003 | Dobrovolny | |
| 6,599,292 B1 | 7/2003 | Ray | |
| 6,602,190 B2 | 8/2003 | Dobrovolny | |
| 6,620,097 B1 | 9/2003 | Bookwalter et al. | |
| 6,659,945 B2 | 12/2003 | Ball et al. | |
| 6,709,389 B2 | 3/2004 | Farascioni | |
| 6,790,177 B2 | 9/2004 | Phillips et al. | |
| 6,808,493 B1 | 10/2004 | Bookwalter et al. | |
| 6,896,654 B2 | 5/2005 | Paolitto et al. | |
| 6,929,606 B2 | 8/2005 | Ritland | |
| 6,951,538 B2 | 10/2005 | Ritland | |
| 7,195,592 B2 * | 3/2007 | Ravikumar et al. | 600/219 |
| 7,207,949 B2 * | 4/2007 | Miles et al. | 600/554 |
| 7,344,495 B2 * | 3/2008 | Ravikumar et al. | 600/219 |
| 7,491,168 B2 * | 2/2009 | Raymond et al. | 600/231 |
| 7,513,869 B2 * | 4/2009 | Branch et al. | 600/210 |
| 7,691,057 B2 | 4/2010 | Miles et al. | |
| 7,819,801 B2 | 10/2010 | Miles et al. | |
| 2002/0007112 A1 | 1/2002 | Rupp et al. | |
| 2003/0097045 A1 | 5/2003 | Kashyap | |
| 2003/0149341 A1 | 8/2003 | Clifton | |
| 2003/0191371 A1 | 10/2003 | Smith et al. | |
| 2004/0087833 A1 * | 5/2004 | Bauer et al. | 600/201 |
| 2004/0129109 A1 | 7/2004 | Phillips et al. | |
| 2004/0176665 A1 | 9/2004 | Branch et al. | |
| 2004/0193018 A1 * | 9/2004 | Thalgott et al. | 600/227 |
| 2004/0225197 A1 | 11/2004 | Roux et al. | |
| 2004/0230191 A1 | 11/2004 | Frey et al. | |
| 2004/0242969 A1 * | 12/2004 | Sherts et al. | 600/231 |
| 2005/0080319 A1 | 4/2005 | Dinkler et al. | |
| 2005/0080320 A1 | 4/2005 | Lee et al. | |
| 2005/0085699 A1 | 4/2005 | Weiss | |
| 2005/0137461 A1 * | 6/2005 | Marchek et al. | 600/220 |
| 2005/0149035 A1 * | 7/2005 | Pimenta et al. | 606/86 |
| 2005/0159650 A1 | 7/2005 | Raymond et al. | |
| 2005/0159651 A1 * | 7/2005 | Raymond et al. | 600/213 |
| 2005/0177028 A1 | 8/2005 | Royce et al. | |
| 2005/0215863 A1 * | 9/2005 | Ravikumar et al. | 600/204 |
| 2005/0215866 A1 * | 9/2005 | Kim | 600/233 |
| 2005/0273133 A1 | 12/2005 | Shluzas et al. | |
| 2006/0030858 A1 | 2/2006 | Simonson et al. | |
| 2006/0052670 A1 | 3/2006 | Stearns et al. | |
| 2006/0052672 A1 * | 3/2006 | Landry et al. | 600/233 |
| 2006/0069315 A1 * | 3/2006 | Miles et al. | 600/219 |
| 2006/0100487 A1 * | 5/2006 | Cartier et al. | 600/232 |
| 2006/0224044 A1 * | 10/2006 | Marchek et al. | 600/233 |
| 2007/0038033 A1 * | 2/2007 | Jones et al. | 600/219 |
| 2007/0073111 A1 * | 3/2007 | Bass | 600/215 |
| 2007/0118022 A1 * | 5/2007 | Hutton | 600/219 |
| 2007/0156024 A1 * | 7/2007 | Frasier et al. | 600/219 |
| 2007/0156025 A1 * | 7/2007 | Marchek et al. | 600/224 |
| 2007/0156026 A1 * | 7/2007 | Frasier et al. | 600/224 |
| 2007/0203399 A1 * | 8/2007 | Gephart et al. | 600/219 |
| 2007/0208227 A1 * | 9/2007 | Smith et al. | 600/219 |
| 2007/0208228 A1 * | 9/2007 | Pavento et al. | 600/233 |
| 2008/0188718 A1 * | 8/2008 | Spitler et al. | 600/213 |
| 2009/0069635 A1 * | 3/2009 | Gephart et al. | 600/224 |

FOREIGN PATENT DOCUMENTS

| | | |
|---|---|---|
| EP | 1466562 | 10/2004 |
| FR | 2570266 | 3/1986 |
| FR | 2788958 | 8/2000 |
| FR | 2807313 | 10/2001 |
| GB | 2107990 | 5/1983 |
| WO | WO0027291 | 5/2000 |
| WO | WO0054663 | 9/2000 |
| WO | WO2005094695 | 10/2005 |

* cited by examiner

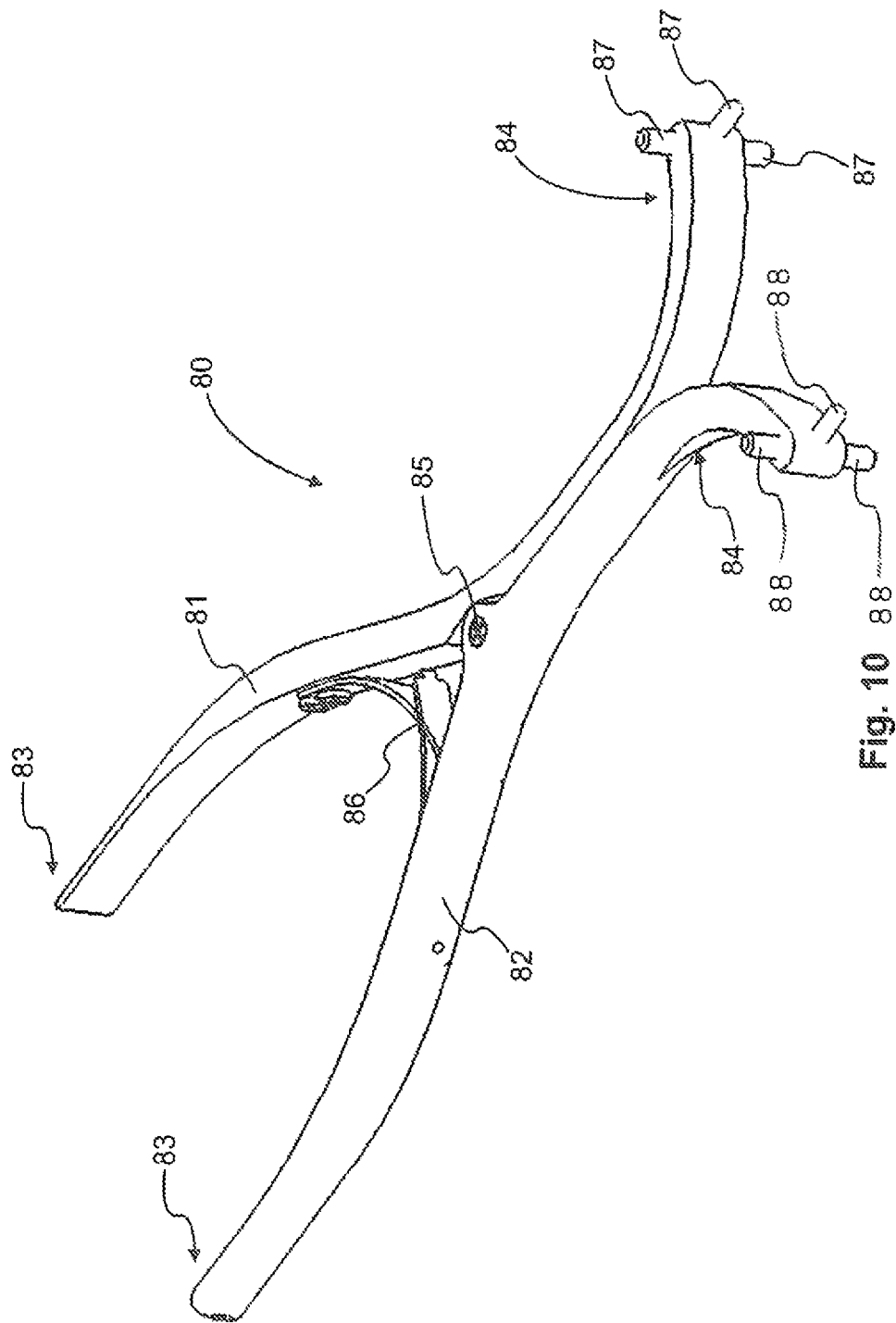

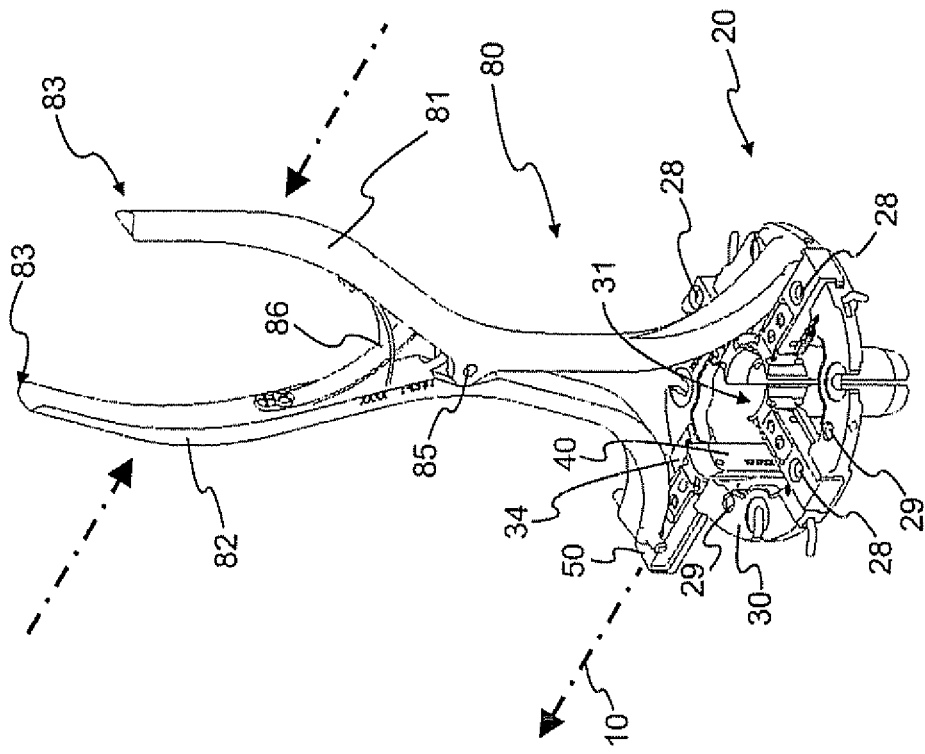
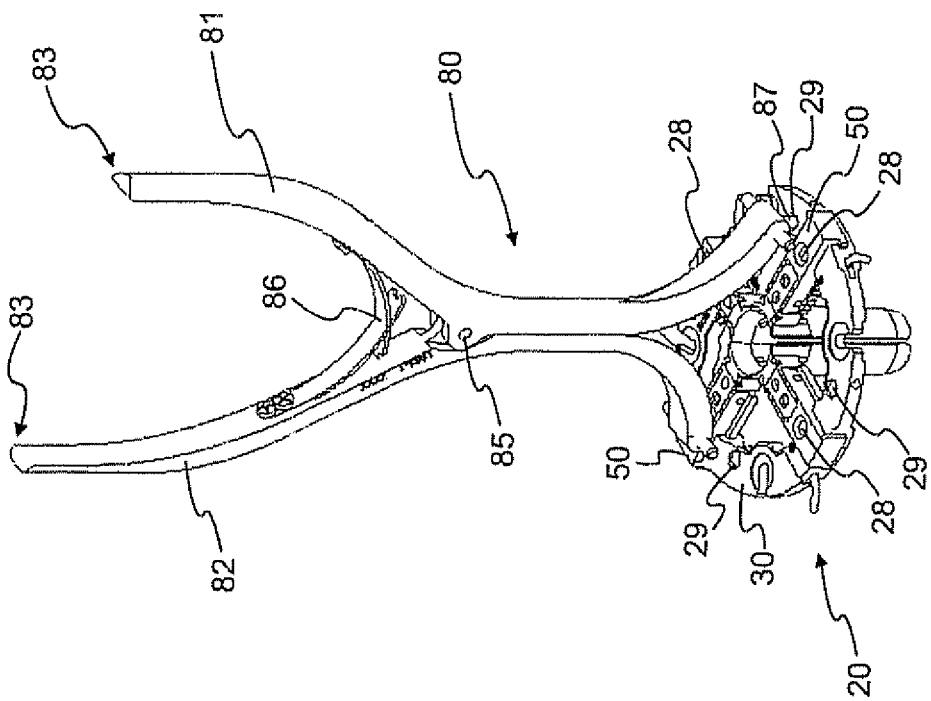

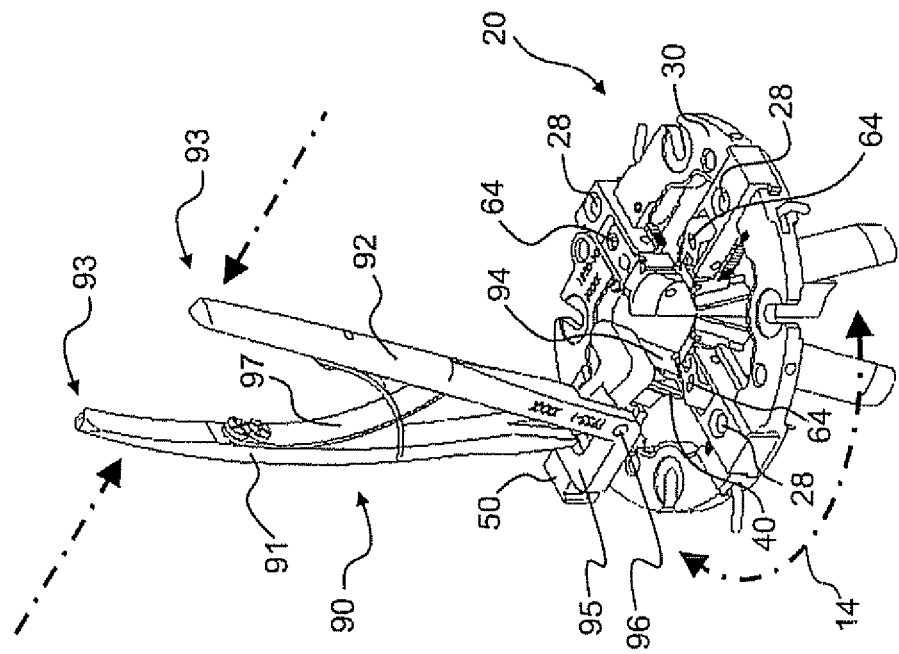
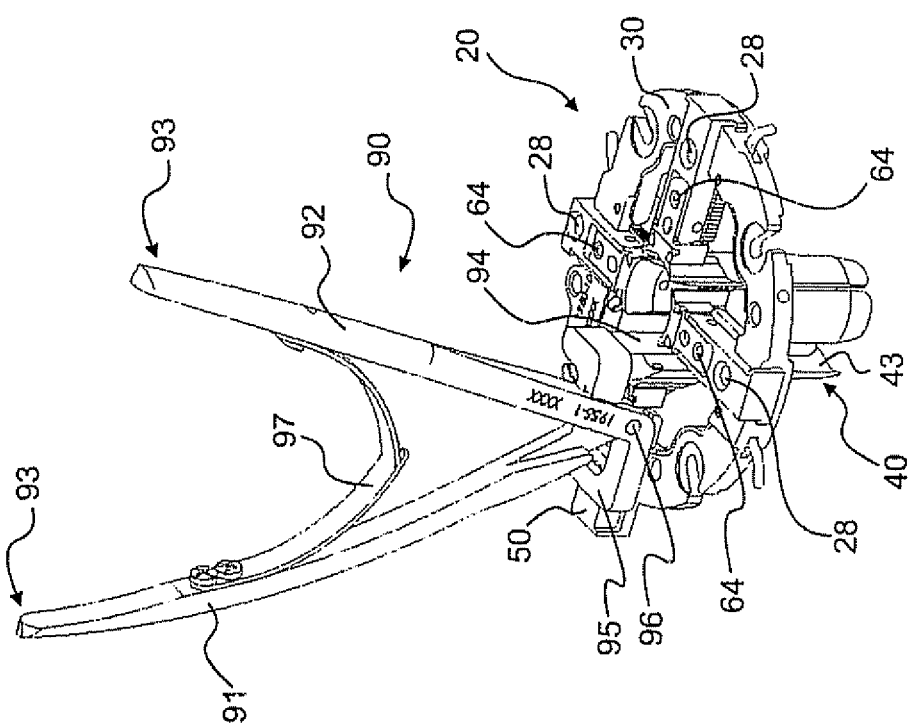

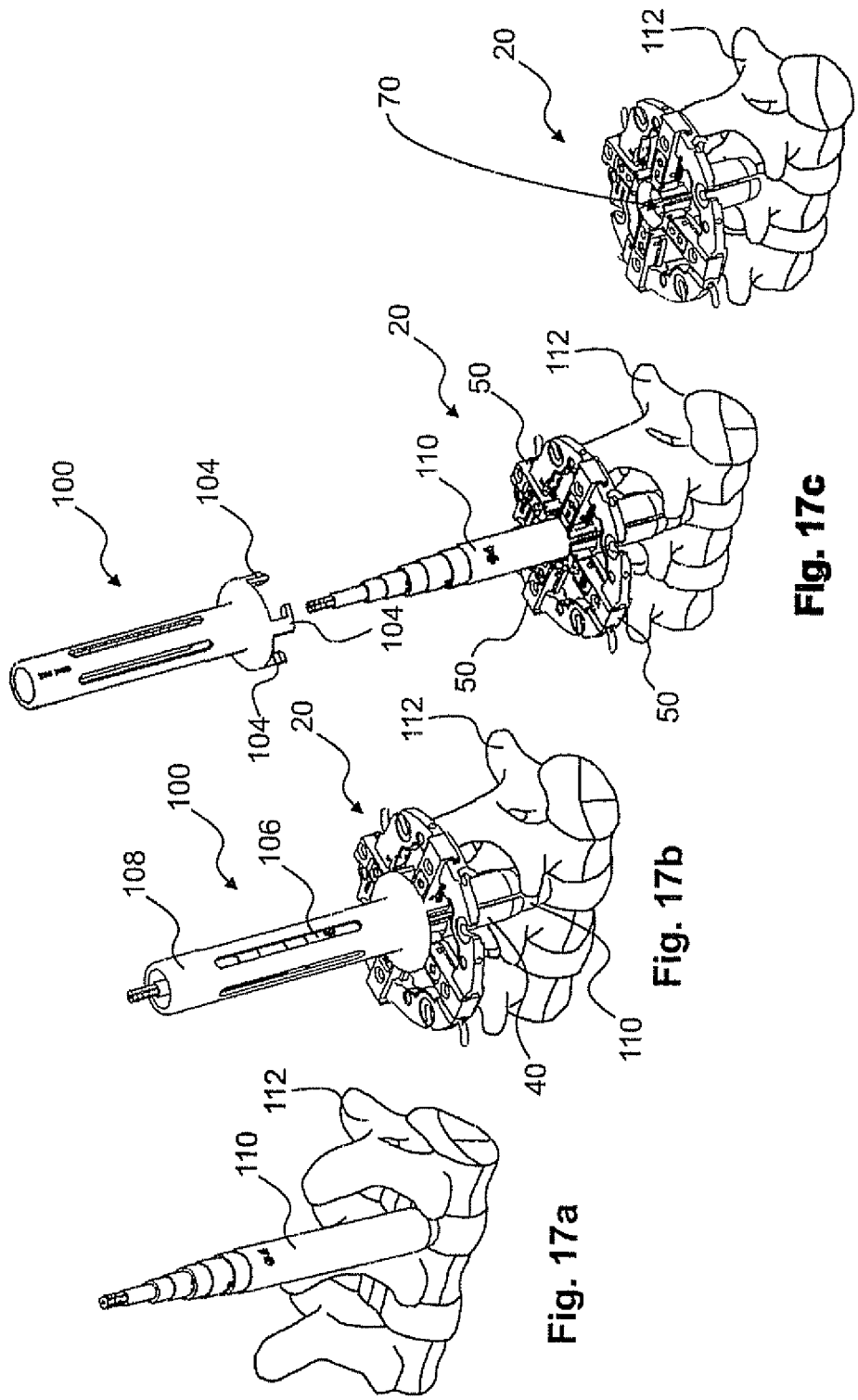

SURGICAL RETRACTOR AND RETRACTOR ASSEMBLY

The present application claims the benefit of U.S. Provisional Application No. 60/780,929, filed on Mar. 8, 2006, which is hereby incorporated in its entirety by reference.

FIELD OF THE INVENTION

The present invention generally relates to a surgical retraction device. Particular embodiments of the invention relate to a retractor device for insertion within an incision of a patient, the retractor including blades configured for independent movement relative the frame of the retractor. Further aspects of the invention include a retractor assembly with one or more tools to facilitate positioning thereof, and related methods.

BACKGROUND OF THE INVENTION

A tissue retractor can be used during a surgical procedure, and in particular during minimally invasive surgical procedures, to temporarily displace tissue and create a working channel to a surgical target site. Such a retractor allows unobstructed access to the target site while limiting the amount of dissection required to reach the target site and reducing trauma to the skin and surrounding tissue. The retractor can be used, for example, to provide unobstructed access to a spinal disc, a vertebra, and/or vertebrae during spinal surgery, such as disclosed in U.S. application Ser. No. 10/937,180 to Landry filed Sep. 9, 2004, which is incorporated herein in its entirety by reference thereto.

A tissue retractor is usually inserted through an incision made in a patient's skin. Insertion can be by blunt insertion, whereby the retractor is simply urged into the incision, or alternatively, insertion can be performed in conjunction with a plurality of dilators, whereby the retractor is inserted over the dilators after sequential dilation of the incision. In either case, insertion of the retractor within the incision can be made difficult due to friction of the skin and tissue against the retractor.

A tissue retractor typically includes a number of retractor blades, which are inserted into an incision made through a patient's skin. After insertion, it is desirable to adjust or move the blade within the incision to retract tissue away from the surgical target depending on the physician's preferences and/or the requirements of the surgical procedure. Movement of the blade within the incision can be difficult due to the tensile forces imparted on the blade by the skin and tissue.

Thus, there remains a need for a retractor or retractor assembly that obviates the disadvantages described above, for example, by allowing a physician to easily insert and adjust the retractor within an incision, and in particular, allowing movement of the retractor blade to a variety of tissue retracting positions.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof as well as from the appended drawings.

The present invention is directed to a retractor for insertion within an incision of a patient. The retractor of a preferred embodiment includes a frame defining a central opening and a reference plane. The retractor also includes at least one blade disposed within the central opening, the blade operatively coupled to the frame by a support structure for movement in a first direction generally lateral with the reference plane between an unretracted position and a retracted position, a second direction at an angle extending through and relative to the reference plane for adjustment of the blade depth, and a third direction rotationally relative to the reference plane. The frame includes a track in mating relationship with the support structure for sliding movement therebetween in a defined relationship relative to the reference plane. In one embodiment, the frame of the retractor has a generally D-shaped configuration.

Preferably, the support structure includes a lateral edge with a dovetail configuration in mating relation with the track. In one embodiment, the retractor also includes a locking mechanism to prevent sliding movement of the support structure relative to the frame when in a locked position. Preferably, the support structure includes a lateral edge with a plurality of teeth defined therein, and the locking mechanism is configured to engage at least one of the plurality of teeth when in the locked position.

In one embodiment, the blade has a distal end portion and a proximal end portion, and the proximal end portion of the blade is coupled with the support structure for sliding movement therebetween in the second direction, such as for adjustment of the blade depth. Preferably, the proximal end portion of the blade includes a dovetail configuration in mating relation with a track disposed on the support structure. The retractor also preferably includes a locking mechanism to prevent sliding movement of the blade relative to the support structure when in a locked position. In one embodiment, the locking mechanism includes a worm gear assembly.

In one embodiment, the blade is pivotally mounted on the support structure by a mounting member for rotational movement in the third direction. Preferably, the mounting member is pivotally connected to the support structure. Also, the retractor can include a locking mechanism to prevent rotational movement of the blade relative the support structure.

The retractor can include a plurality of blades disposed within the central opening, and each blade is preferably operatively coupled to the frame by a corresponding support structure for movement in the first direction, the second direction and the third direction, respectively. Each blade preferably includes an inwardly-facing surface and a pair of lateral edges, and each inwardly-facing surface preferably defines a portion of a working channel formed when the blades are in an unretracted position with the lateral edges of adjacent blades disposed proximate each other. Preferably, the working channel has a central axis defined therethrough, and each blade is preferably capable of being moved from the unretracted position in the first direction away from the central axis and has a distal end portion that is preferably capable of being rotated in the third direction away from the central axis.

The present invention is also directed to a retractor assembly comprising a retractor in combination with one or more tools. For example, the retractor assembly can include a retractor in combination with an adjustment tool. The adjustment tool generally includes a first arm removably engageable in a fixed location relative to the blade, and a second arm removably engageable for movement with the blade, the second arm movable relative to the first arm to move the blade selectively relative the reference plane. Preferably, the first arm is hinged relative the second arm. Also, the first arm and second arm are preferably biased away from each other.

In one embodiment, the adjustment tool includes a first engagement portion on the first arm and a second engagement portion on the second arm, and the first engagement portion is engageable with the frame of the retractor. Preferably, the frame includes a recess to receive the first engagement portion. The second engagement portion of the adjustment tool is preferably engageable with the support structure to move the blade in the first direction. Preferably, the support structure includes a recess to receive the second engagement portion.

In another embodiment, the first engagement portion on the first arm is engageable with the support structure and the second engagement portion on the second arm is engageable with the blade to move the blade in the third direction. Preferably, the support structure includes a recess to receive the first engagement portion, and the second engagement portion is preferably configured to engage an inwardly-facing surface of the blade.

In another preferred embodiment of the retractor assembly, an insertion tool is provided. The insertion tool includes a tubular member having a distal end and a proximal end, and a coupling structure at the distal end of the tubular member to removably engage the retractor proximate the blade.

In one embodiment, the coupling structure includes a finger configured to engage the support structure. Preferably, the finger has an L-shape configured to engage the support structure upon rotation of the insertion tool relative to the retractor. The finger preferably inhibits movement of the blade at least in one of the first direction, second direction and third direction, although more preferably, the finger inhibits movement of the blade in each of the first direction, second direction and third direction.

In another embodiment, the retractor assembly further comprises a plurality of dilators configured for sequentially dilating tissue within an incision, and the insertion tool preferably has an inner channel defined therethrough with a cross dimension sized to receive at least a portion of the plurality of dilators therein. Preferably, the insertion tool includes at least one viewing port defined therein to allow visual inspection of the dilators therein.

The present invention is also directed to methods of inserting positioning a retractor using the tools previously described. The present invention thus describes a retractor and retractor assembly that enables a physician to insert and adjust the retractor more readily within an incision. Additionally, the present invention describes a method of use for insertion and adjustment of the retractor within the incision.

It is to be understood that both the foregoing general description and the following detailed description are exemplary and are intended to provide further explanation of the claimed invention.

The accompanying drawings, which are incorporated in and constitute part of this specification, are included to illustrate and provide a further understanding of the invention. Together with the description, the drawings serve to explain the principles of the invention.

BRIEF DESCRIPTION OF THE DRAWINGS

FIG. 3a depicts a perspective view of a representative embodiment of a support structure and a mounting member coupled thereto;

FIG. 3b depicts a top view of the support structure of FIG. 3a;

FIG. 10 depicts a perspective view of a representative embodiment of a distractor tool in accordance with another aspect of the invention;

FIG. 11a depicts a perspective view of the distractor tool of FIG. 10 engaged in a first orientation with a frame and support structure of a retractor;

FIG. 11b depicts a perspective view of the retractor assembly of FIG. 11a with the handles of the distractor tool moved toward the compressed position to distract the corresponding blade;

FIG. 14a depicts a perspective view of the pivot tool of FIG. 13 engaged with a blade and support structure of a retractor;

FIG. 14b depicts a perspective view of the retractor assembly of FIG. 14a with the handles of the pivot tool moved toward the compressed position to pivot the corresponding blade;

FIGS. 17a-d schematically depict selected views of a method of inserting the retractor assembly of FIG. 16a.

DETAILED DESCRIPTION OF THE PREFERRED EMBODIMENTS

Reference will now be made in detail to presently preferred embodiments of the invention, examples of which are illustrated in the accompanying drawings. Methods of using the retractor assemblies of the invention are described in conjunction therewith.

In accordance with the invention, a retractor is provided for insertion within an incision of a patient. The retractor includes a frame generally defining a central opening and a reference plane. At least one blade is disposed within the central opening, and operatively coupled to the frame by a support structure for movement in a first direction generally laterally with or across the reference plane between an unretracted position and a retracted position, a second direction at an angle extending through and relative to the reference plane for adjustment of the blade depth, and a third direction rotational relative to the reference plane. In accordance with a further aspect of the invention, the frame includes a track in mating relationship with the support structure for sliding movement therebetween in a defined relationship relative to the reference plane.

Figure 1:
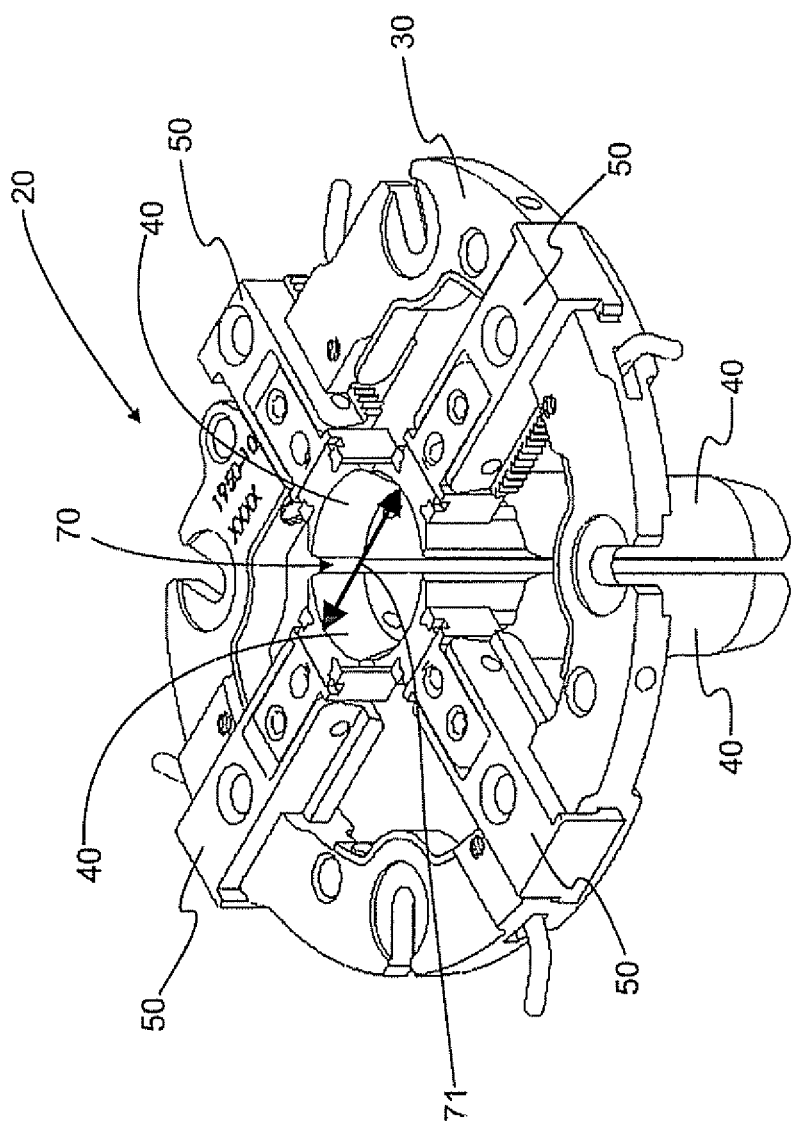
FIG. 1 depicts a perspective view of a representative embodiment of a retractor with four blades in the unretracted position.

For the purpose of illustration and not limitation, reference is made to the representative embodiment of the retractor shown in FIG. 1. A retractor 20 is configured for insertion within an incision to temporarily displace obstructing tissue and create a channel to gain access to a surgical target site, among other things. The retractor 20 can be used to retract or otherwise displace skin, muscle, tissue, organs, bone, blood vessels, connective tissue, nerve tissue, or the like. The retractor 20 generally includes a frame 30 and blades 40, each coupled to the frame 30 by a support structure 50.

Figure 2:
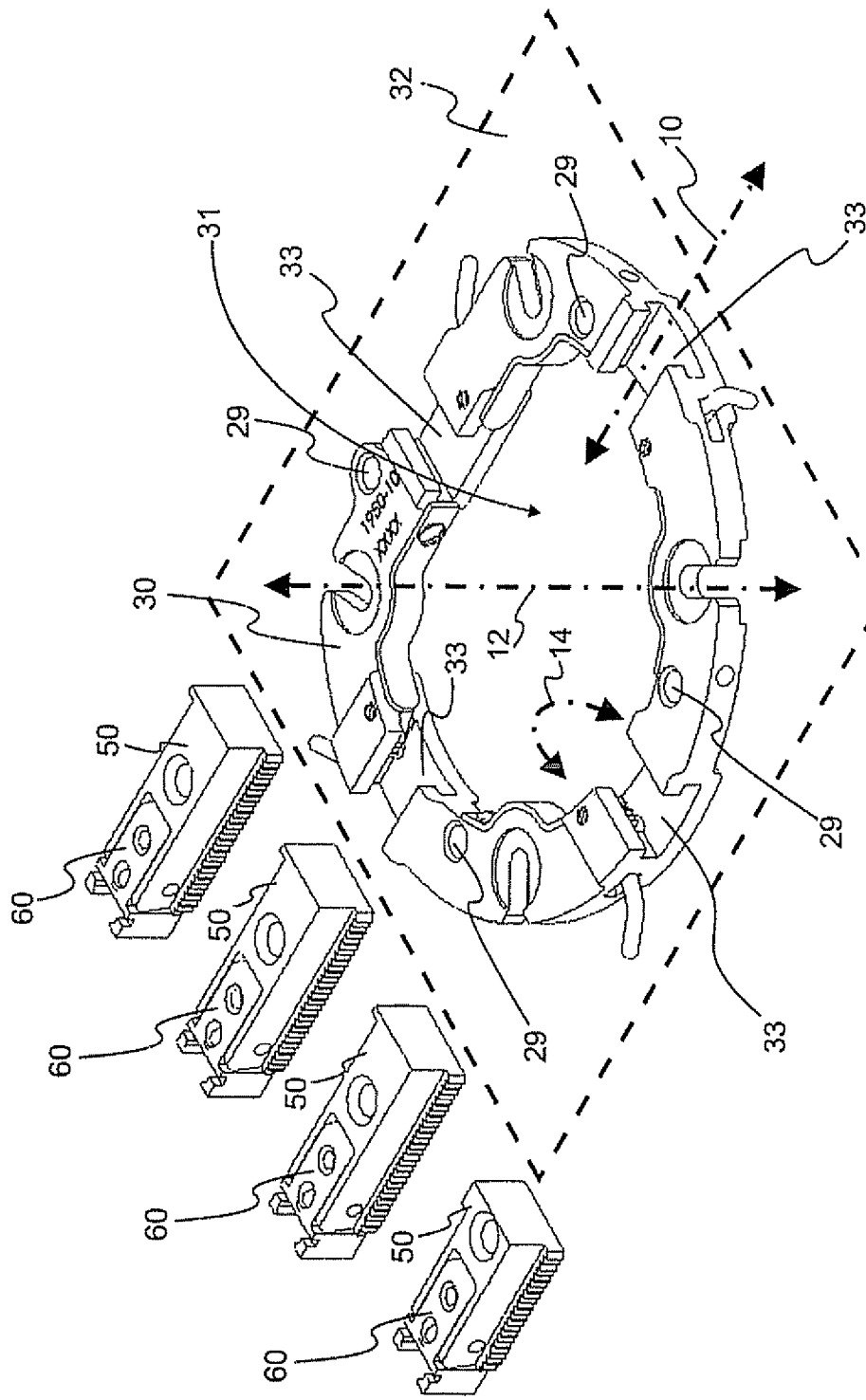
FIG. 2 depicts a perspective view of a representative embodiment of a frame and a variety of support structures.

As embodied herein, for purpose of example and not limitation, the frame 30 has a D-shaped configuration that defines a central opening 31 within the frame. The D-shape configuration is advantageous for posterior indications, with the straight side of the D-shaped frame aligned along a length of the spine. In other embodiments, the frame can have an alternative configuration depending on its desired use and application. For example, the frame can be generally circular, elliptical, oval, rectangular, or asymmetric shape. Furthermore, and as previously noted, the frame generally defines a reference plane. For example, and for purpose of illustration, the frame 30 embodied herein is depicted with a generally planar configuration that defines reference plane 32 in which the frame 30 lies, as shown in FIG. 2. However, the frame likewise can have an angled, arcuate or curved shape and still define a reference plane, such as an imaginary plane extending through any desired reference point on the frame.

The retractor can include one or more moveable blades, although a plurality of blades are preferred. While the retractor 20 of FIG. 1 includes four blades 40, any number of blades can be coupled to the frame. As embodied herein, each blade is coupled to the frame by a support structure 50. With regard to the D-shaped frame embodied herein, for purpose of illustration, three of the support structures 50 are of equal length, and the fourth support structure 50 is shorter in length. In this manner, the shorter support structure 50 is preferably configured to couple to the D-shaped frame 30 adjacent the straight portion thereof. Each support structure 50 generally has an elongate configuration, with a proximal end portion, a distal end portion and a lateral edge extending therebetween. The length of the support structures can vary depending upon the dimensions of the frame, the number of blades to be used, and the intended applications, among other things. Although depicted with a rectangular cross-section, the support structures can be generally oval or elliptical, or have any other cross-section or configuration depending on the requirements of the application or surgical procedure. Furthermore, the support structures of different configurations and lengths preferably interchangeable with each other, such that a kit can be provided with a variety of support structures, if desired.

As described in detail below, coupling of each blade 40 to the frame 30 by support structures 50 in accordance with the invention allows the blades 40 to move in a first direction 10 generally laterally across or with the reference plane 32, as depicted for purpose of illustration by arrow 10 in FIG. 4. In accordance with one aspect of the invention, the frame includes a track in mating relationship with the support structure for sliding movement therebetween. Preferably, the track is configured to ensure a defined or predetermined relationship of movement of the support structure relative to the reference plane. As embodied herein, four tracks are provided. Although a variety of track configurations and arrangements are possible. FIG. 1 depicts the tracks in radial alignment relative to central axis, with pairs of tracks opposing each other.

Figure 3:
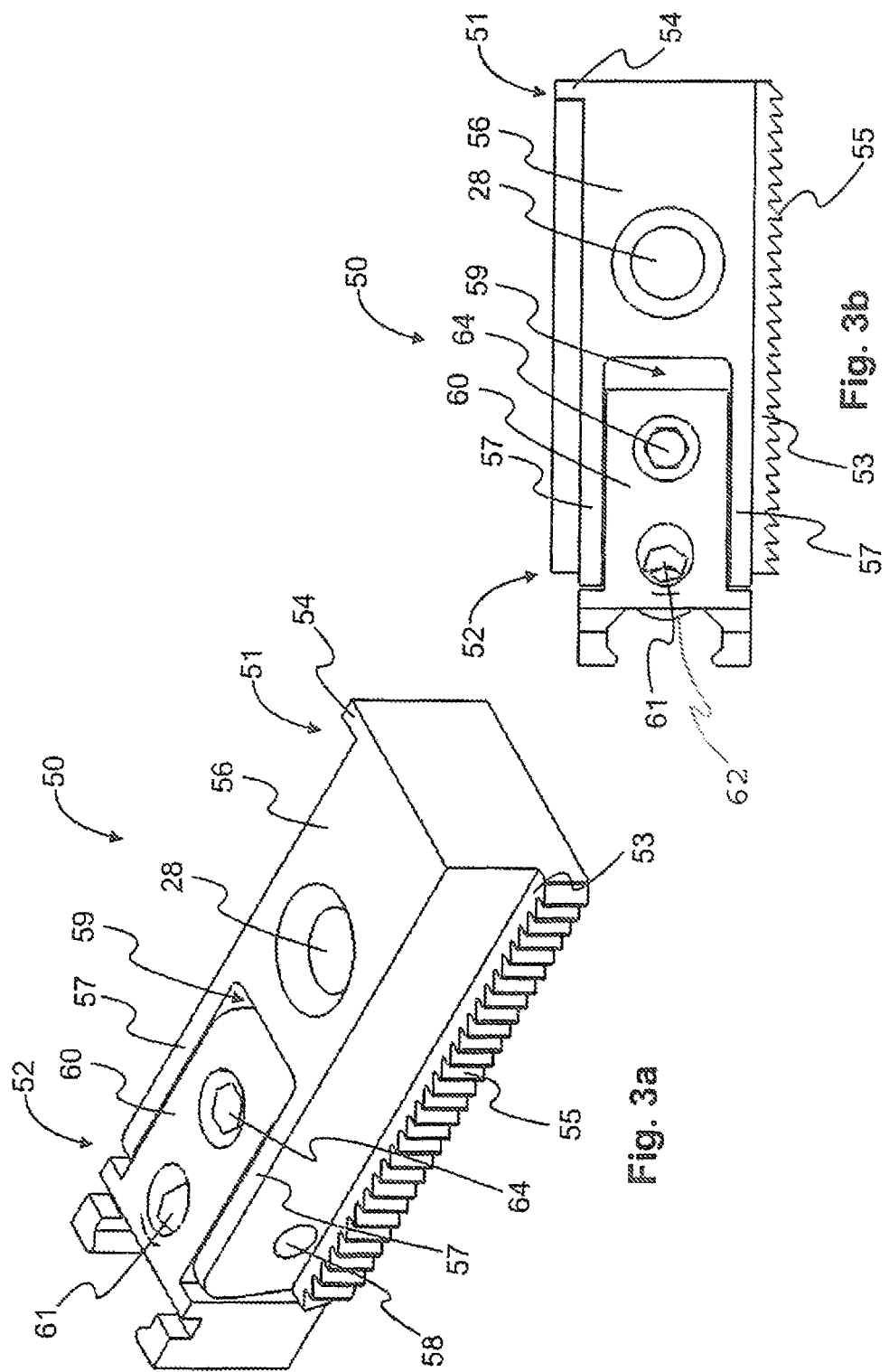

As embodied in FIGS. 3*a* and 3*b*, each support structure 50 includes a distal end portion 51 and a proximal end portion 52. Mating engagement is accomplished, in this embodiment, by a dovetail configuration along a lateral edge 53 the support structure is that is configured to matingly engage within the track in the from of receiving slot 33 disposed along the surface of the frame 30, the receiving slot 33 configured to receive the lateral edge 53 therein. Hence, each support structure 50 can slide relative to the frame 30 in the first direction 10 in a fixed or predetermined relationship relative to the reference plane, as shown in FIG. 4. For example, FIG. 4 depicts the fixed relationship as being parallel with the reference plane, although an angled relationship is also possible. Preferably, the support structure 50 includes an abutment portion 54 disposed proximate the distal end portion 51 thereof. The abutment portion 54 is configured to engage a portion of the frame 30 when the support structure 50 slides in the first direction 10 toward the central opening 31 to prevent the distal end portion 51 of the support structure 50 from sliding unobstructed completely through the track. Other embodiments can include different configurations to engage the support structure with the frame to provide movement in the first direction in a fixed relationship with the reference plane.

The retractor preferably also includes a locking mechanism to prevent sliding movement of the support structure at least toward the unretracted position relative to the frame when in a locked position. For example, the support structure includes a lateral edge with a plurality of teeth defined therein. The locking mechanism is configured to engage at least one of the plurality of teeth when in the locked position.

Figure 4:
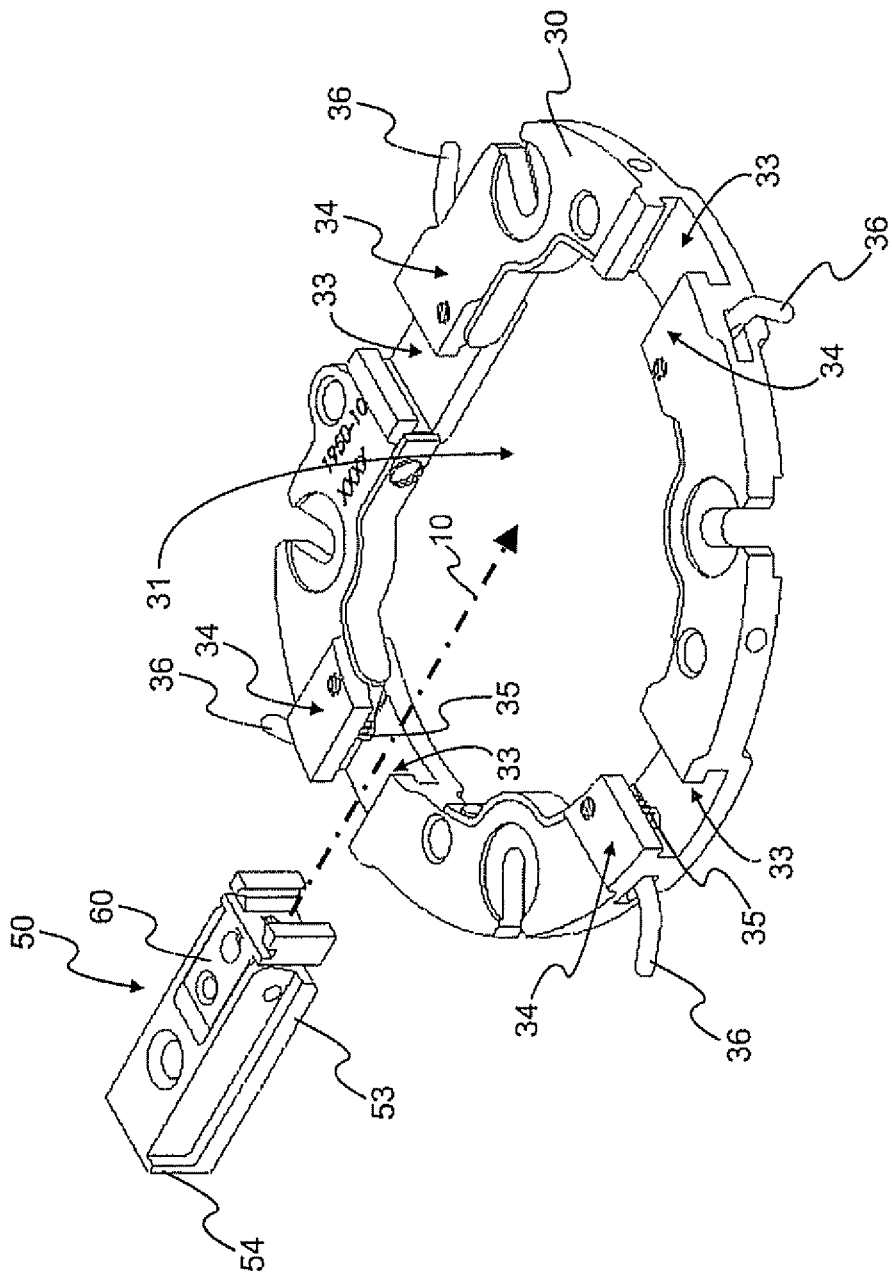
FIG. 4 depicts an exploded view of the engagement a support structure with the frame.

As embodied herein and with reference to FIG. 4, a lateral edge 53 of the support structure 50 includes a plurality of teeth 55 configured for engagement with a locking mechanism 34 on the frame 30. Preferably, the locking mechanism 34 includes a protrusion 35 disposed proximate the receiving slot 33 and configured to engage at least one tooth 55 of the lateral edge 53. In a preferred embodiment, the locking mechanism 34 also includes an adjusting or activating handle 36, which is configured to adjust the locking mechanism 34 to a locked position such that the protrusion 35 engages the teeth 55 of the lateral edge 53. Upon engagement, the support structure 50 is prevented from sliding in the first direction 10 toward the unretracted position. If desired, the locking mechanism can be configured to allow movement toward the retracted position even when locked, or to prevent any movement if preferred. Upon release of the locking mechanism 34 from the locked position, movement of the support structure 50 along the first direction 10 is restored. In other embodiments, the locking mechanism can be biased to automatic activation can have other configurations to prevent movement of the support structure in the first direction.

Figure 5:
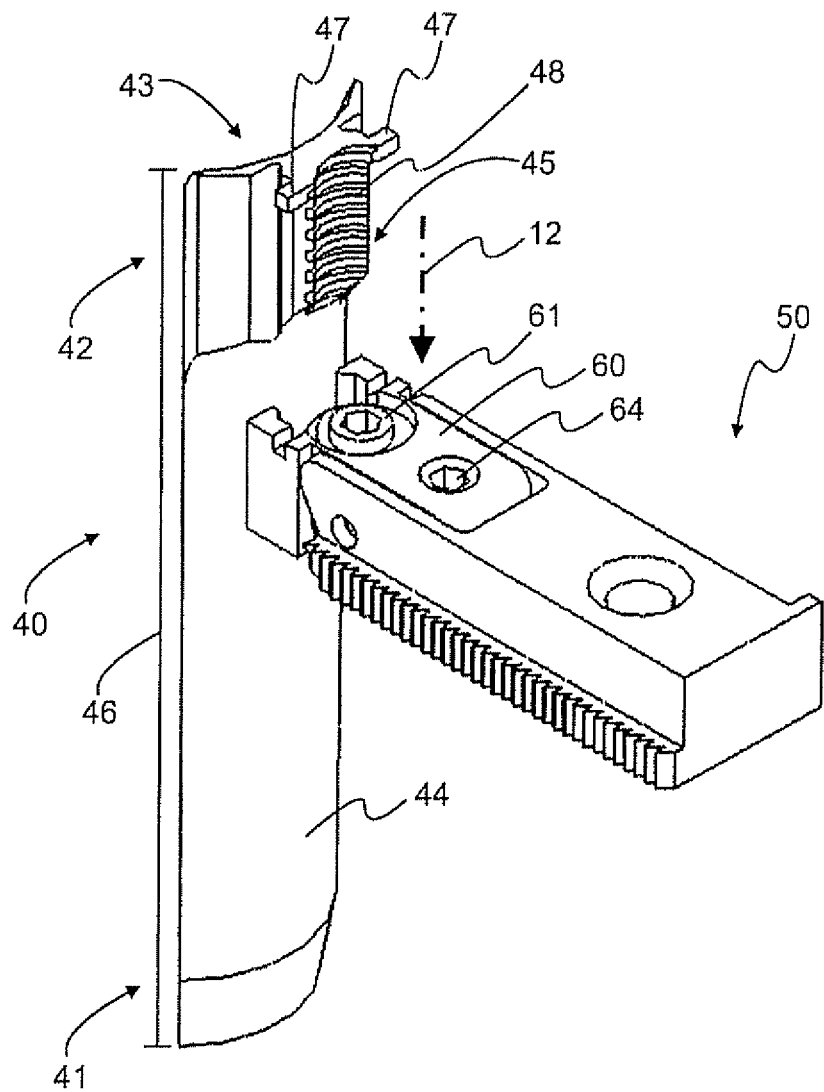
FIG. 5 depicts an exploded view of the engagement of a blade with the support structure.
Figure 7:
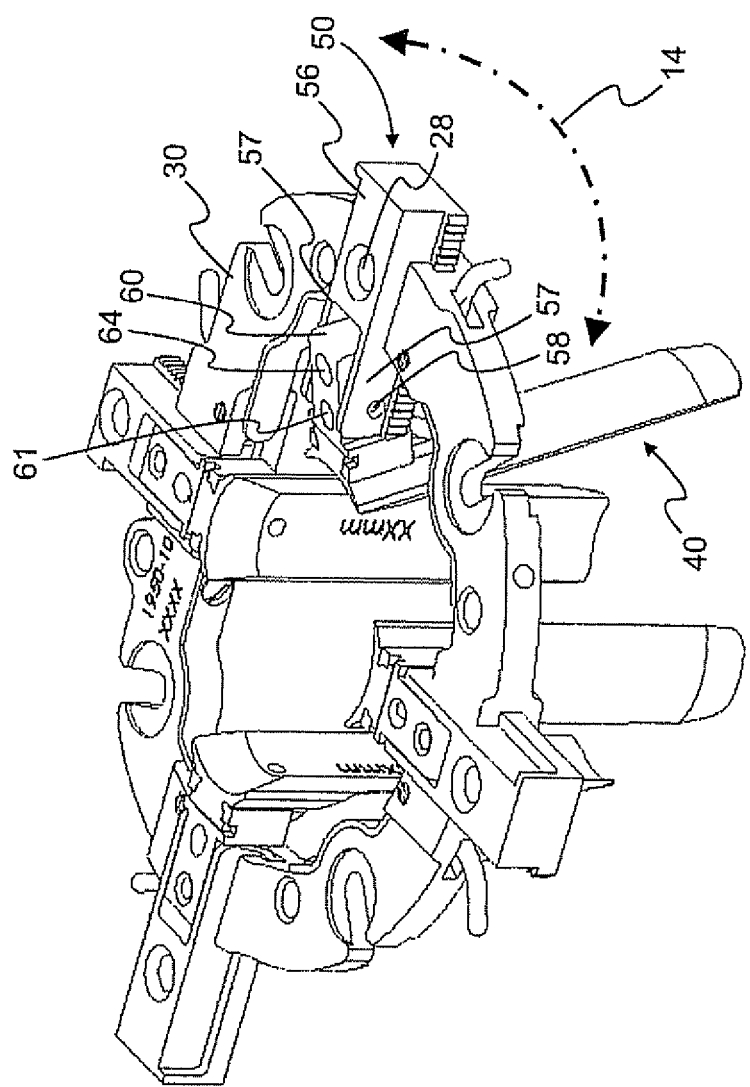
FIG. 7 depicts a perspective view of the rotational adjustment of the blade.

Coupling of each blade to a support structures of appropriate configuration also allows the blade to move in a second direction extending through and at an angle relative to the reference plane 32 for adjustment of the relative blade depth as depicted for purpose of illustration by arrow 12 in FIG. 5, and in a third direction rotational relative to the reference plane 32 as depicted by arrow 14 in FIG. 7. For example, and as shown in the embodiment of FIG. 1, each blade 40 is coupled to the frame 30 by the support structures 50 such that the blades are disposed within the central opening 31, preferably extending at an angle to the reference plane 32. Although shown as orthogonal to the reference plane, the angle of the second direction relative the reference plane can be adjusted or altered by movement of the blade in the third direction.

Each support structure 50 includes a mounting member 60, which is pivotally coupled at one end to the support structure 50. The opposite end of each mounting member 60 is configured to matingly engage a portion of a respective blade 40. Each blade preferably has a distal end portion and a proximal end portion. The proximal end portion of the blade is coupled with the support structure for sliding movement therebetween in the second direction, such as for adjustment of the relative blade depth. For example, and as embodied herein, the proximal end portion of the blade includes a dovetail configuration in mating relation with a track disposed on the support structure as described further below.

As shown in the embodiment of FIG. 5, each blade 40 has a distal end portion 41 and a proximal end portion 42 that defines a blade length 46. Preferably, the blades of the retractor have equal lengths 46. The distal end 41 preferably has a tapered configuration to facilitate insertion of the blade 40 within an incision. The length 46 of each blade is generally between about 20 mm and about 200 mm. For example, blades for posterior spinal approaches can range in length from about 20 mm to about 80 mm, and blades for anterior spinal approaches or lateral spinal approaches can range in length from about 70 mm to about 200 mm.

Furthermore, each blade preferably includes an inwardly-facing surface and a pair of lateral edges. Each inwardly-facing surface defining a portion of a working channel formed when the blades are in an unretracted position with the lateral edges of adjacent blades disposed proximate each other. Preferably, the working channel has a central axis defined therethrough and each blade is capable of being moved from the unretracted position in the first direction away from the central axis and has a distal end that is capable of being rotated in the third direction away from the central axis.

Figure 6A:
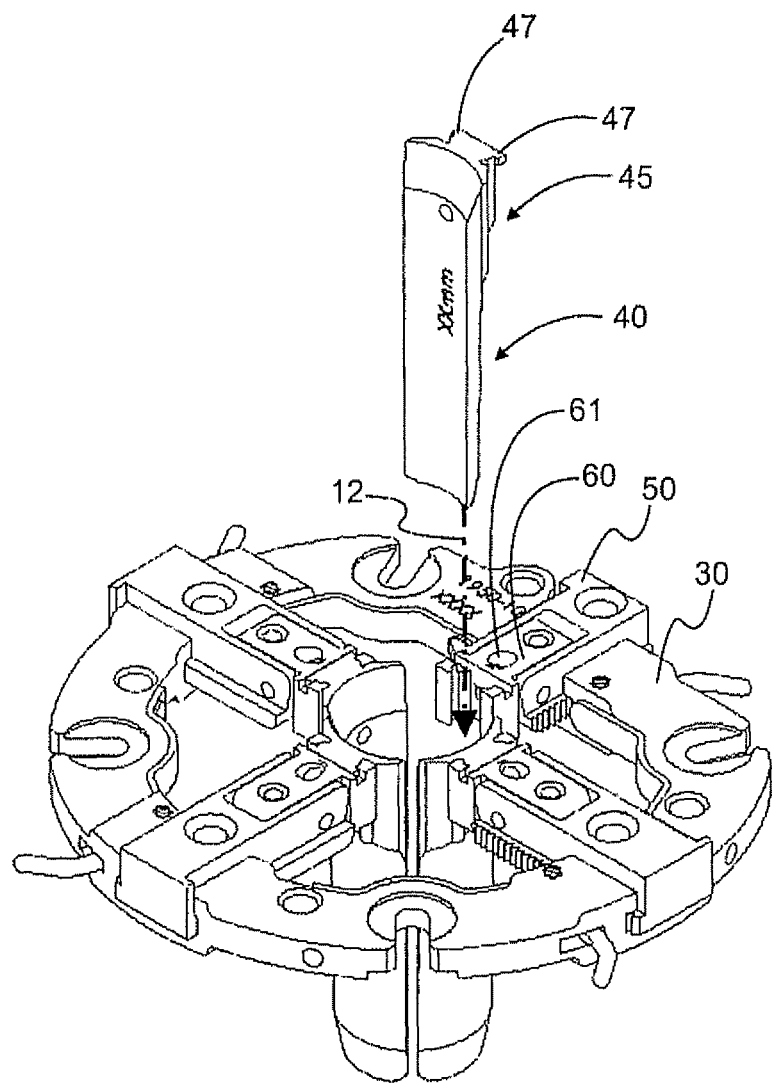
FIG. 6a depicts an exploded view of the engagement of a blade with the support structure coupled to a frame.

For example, and as depicted in FIG. 6a, extending between the distal and proximal ends 41,42 and along the blade length 46 is an inward-facing blade surface 43, preferably having a convex or curved configuration. More preferably, the curved surface 43 substantially complementary to the curvature of a dilator that is used to provide initial dilation of the incision. Opposite the inward-facing surface 43 is a retraction surface 44 that is configured to contact and retract skin and tissue. In some embodiments, the blade can include a slot that runs along the length of the blade such that during a surgical procedure, a scalpel or other cutting instrument can be inserted through slot to further cut or extend the incision without removing the retractor from the patient. In other embodiments, the blades can be of varying lengths and configurations, depending on the desired use and application of the retractor.

Each blade 40 also includes a coupling portion disposed at the proximal end 42 of the blade. As embodied herein, the coupling portion 45 is disposed adjacent the retraction surface 44 of the blade, and has a dovetail configuration. Preferably, the coupling portion 45 is configured to matingly engage the mounting member 60 of the support structure 50, which is configured to receive the dovetail coupling portion 45 therein. This allows the blade 30 to slide relative to mounting member 60 and support structure 50 in the second direction 12 for depth adjustment of the blade. Other embodiments can include different configurations to engage the blade with the support structure to provide movement in the second direction.

Figure 6B:
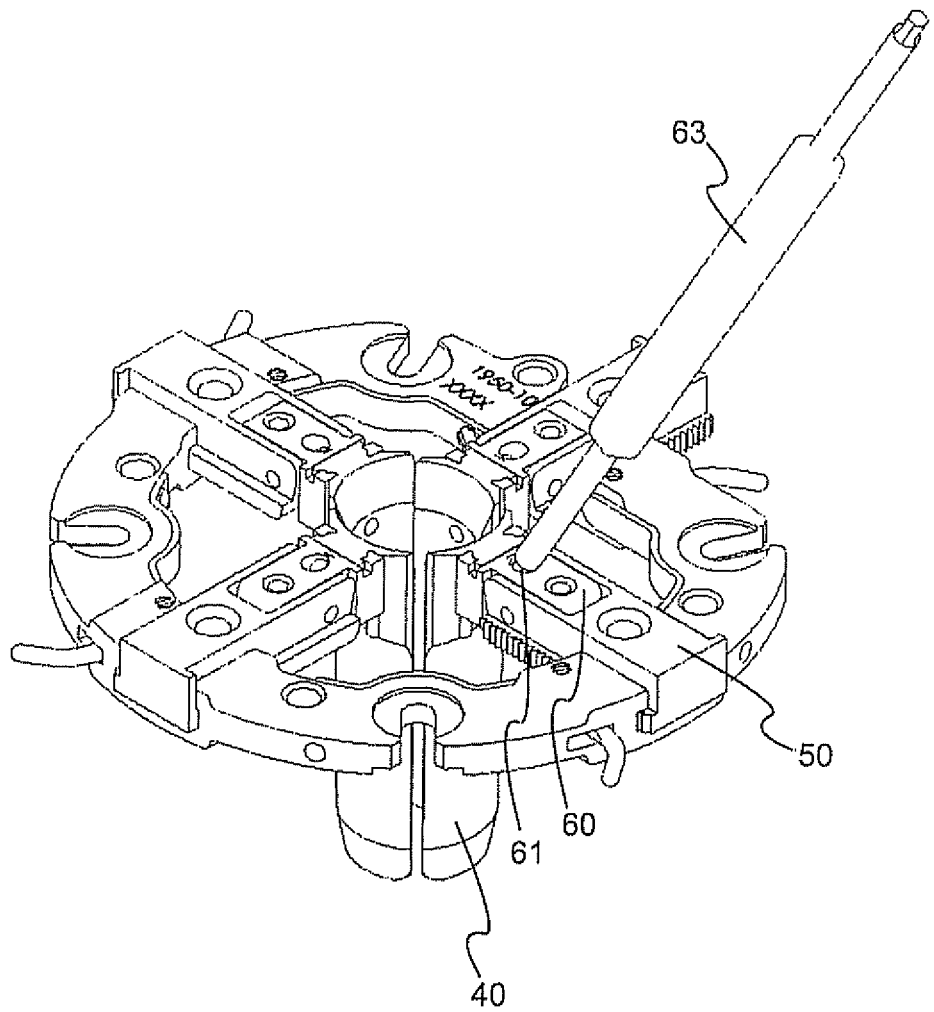
FIG. 6b depicts a perspective view of the height adjustment of a blade using an adjustment tool.

Preferably, the retractor includes locking mechanism to prevent sliding movement of the blade relative to the support structure. More preferably, the locking mechanism is an adjustable mechanism, such as a worm gear assembly or the likes. As embodied in FIG. 5, the locking mechanism 61 includes a worm gear 62 (shown in FIG. 3b) at least partially disposed on the mounting member 60 to receive the dovetail coupling portion 45 of the blade therein. The coupling portion 45 preferably has threaded or toothed surface 48 configured for engagement with the worm gear 62. In this configuration, the worm gear 62 facilitates an adjustable association of the coupling portion 45 of the blade 40 with the mounting member 60 as the worm gear 62 engages the threaded surface 48 of the coupling portion 45. Upon rotation of the worm gear 62, the coupling portion 45 and the blade 40 move along the second direction, as shown in FIG. 6a. Preferably, the engagement between the worm gear 62 and the threaded surface 48 of the coupling portion 45 is under high torque such that the blade 40 is inhibited from movement in the second direction without intentional rotation of the worm gear 62 or an overriding force applied to the blade. As embodied herein, rotation of the worm gear 62 requires use of a leverage tool 63 that is configured to associate with worm gear 62 and rotate the worm gear 62 upon rotation of the tool 63, as shown in FIG. 6b. In other embodiments, the locking mechanism can have other configurations to prevent movement of the blade in the second direction or depth, such as a ratchet assembly or the like.

Preferably, the proximal end of the coupling portion 45 includes an abutment portion 47 configured to engage a portion of the mounting member 60 when the coupling portion 45 slides along the second direction 12 toward the target site. The abutment portion 47 prevents the proximal end of the coupling portion 45 from sliding completely through the mounting member 60 toward the target site.

In contrast, and as embodied herein, the coupling portion 45 preferably does not include an abutment portion to prevent the coupling portion 45 from being removed from the mounting member 60 along the second direction 12 away from the target site. Thus, movement in the second direction not only allows for depth adjustment, but also permits the blade 40 to be completely removed from engagement with a mounting member 60 when desired. This advantageously allows an individual blade to be removed and replaced with another blade of the same or different length or configuration, depending on its desired use and application. As embodied herein, each blade 40 can be removed and replaced while the retractor 20 is inserted within the incision.

Preferably, the blade is pivotally mounted on the support structure by a mounting member for rotational movement in the third direction. For example, and with reference to the embodiment lever, the mounting member can be pivotally connected to the support structure. Additionally, the retractor preferably includes a locking mechanism to prevent rotational movement of the blade relative the support structure. As shown in the embodiment of FIGS. 3a, 3b, and 7, the mounting member 60 is coupled to the support structure 50. Preferably, the mounting member 60 is pivotally coupled to one end of the support structure 50. This allows the mounting member 60 and the blade 40 coupled thereto to pivot relative to the support structure 50 in the third direction 14. As embodied herein, the support structure 50 includes a body 56 having a pair of arms 57 extending therefrom. The extending aims 57 define a receiving area 59 therebetween. The mounting member 60 is received in the receiving area 59 between the arms 57, and coupled to the extending arms 57 by an axle or pivot pins 58 for rotational engagement. In this configuration, the mounting member 60 can pivot about the pivot pins 58 to rotate the blade 40 in the third direction 14 relative to the support structure 50. Preferably, the blade 40 can rotate between a first position, where the blade 40 is disposed at an angle of about 90° relative to the reference plane 32, and a second position, where the blade 40 is disposed at an angle of about 30° or even less if desired relative to the reference plane 32. Other embodiments can include different configurations to engage the blade with the support structure to provide rotation in the third direction.

Preferably, movement of the mounting member 60 relative to the support structure 50 in the third direction 14 is controlled by a locking mechanism. As embodied herein, the mounting member 60 includes a locking mechanism 64 configured to engage the pivot pins 58 such that upon engagement therewith, rotation of the mounting member 60 about the pivot pins 58 in the third direction 14 is inhibited. Upon disengagement of the locking mechanism 64 with the pivot pins 58, rotation of the mounting member 60 in the third direction 14 is restored. In one preferred embodiment, the locking mechanism 64 is an adjustable set screw configured for movement between locked and unlocked positions upon rotation by the leverage tool 63. In other embodiments, the locking mechanism can have other configurations, such as to allow for fine adjustments of the mounting member in the third direction upon rotation of the locking mechanism. After coupling the blade 40 with the mounting member 60, the blade 40 can be advantageously rotated to and fixed in a variety of angles relative to the support structure 50 to retract skin and tissue away from the target site.

As described further below, the frame also preferably includes at least one tool engagement portion disposed about the surface of the frame and configured for engagement with a tool. For example, and as embodied herein, the frame 30 includes four recesses 29 disposed about the surface of the frame 30. Each recess 29 is configured for engagement with a tool that is configured to move each of the blades 40 relative to the frame 30. The tool and its engagement with the recesses 29 of the frame 30 are described in more detail below. Likewise, each support structure 50 also preferably includes a tool engagement portion disposed on the surface thereof and configured for engagement with a tool. As embodied herein, each support structure 50 includes a recess 28 disposed on the surface of the body 56. The recess 28 is preferably configured for engagement with tools that are configured to move the blade 40 relative to the frame 30. The tools and their engagement with the recess 28 of the support structure 50 are described in more detail below.

The retractor 20 and its components (e.g., the frame 30, the blades 40, the support structures 50, and the mounting members 60) as previously described are preferably assembled prior to insertion of the retractor 20 within the incision. Preferably, each of the support structures 50 of the assembled retractor 20 is moved to an unretracted position with each support structure 50 moved in the first direction 10 toward the central axis of the opening 31. In the unretracted position, each of the blades 40 extending from the support structures 50 define a working channel 70 within the central opening 31, as shown in FIG. 1. As embodied herein, the working channel 70 has a generally circular configuration defined by curved inward-facing surfaces 43 of each of the blades. Preferably, the abutting surfaces of the support structures prevent the blades from being positioned with the lateral edges of the blades 40 in engagement with each other so as to define a gap between the adjacent blades. In other embodiments, the lateral edges of adjacent blades can be positioned to engage one another to formed a closed working channel 70.

Preferably, the circular working channel 70 has a diameter 71 configured to receive a plurality of nested tissue dilators therethrough. Upon removal of the dilators, the diameter 71 of the working channel 70 is preferably large enough to provide an unobstructed view to the surgical target site, and allow manipulation of surgical tools therethrough to perform a surgical procedure. Alternatively, the blades of the retractor can be retracted as desired to increase the working space.

In accordance with another aspect of the invention, a tool is provided to assist with inserting the retractor within the incision. Preferably, the tool includes a tubular member having a distal end and a proximal end, and a coupling structure at the distal end of the tubular member to removably engage the retractor proximate at least one blade.

Figure 15:
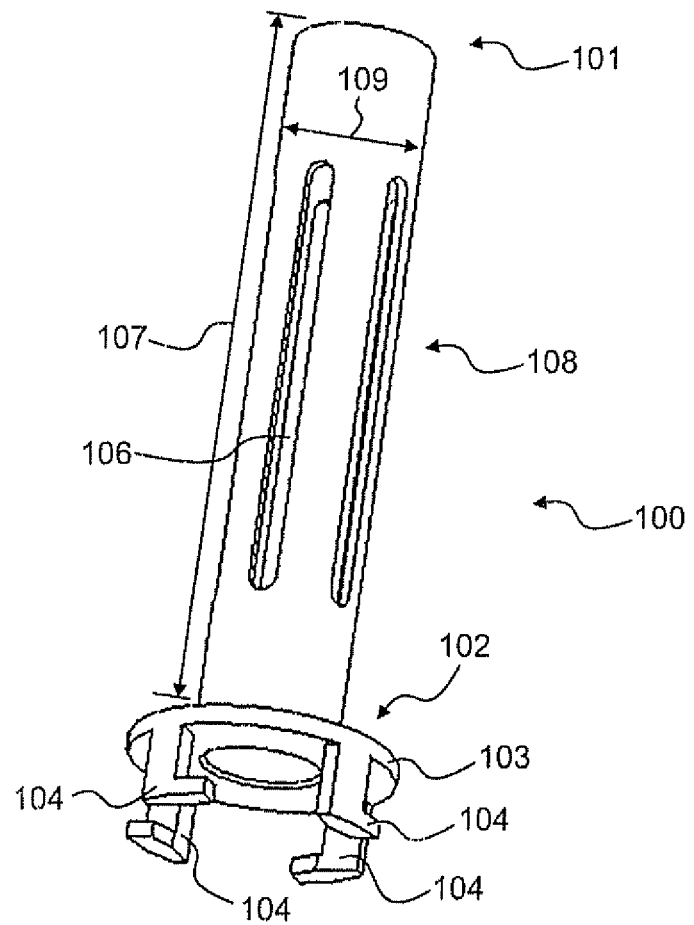
FIG. 15 depicts a perspective view of a representative embodiment of an insertion tool.

As embodied in FIG. 15, the tool is an insertion tool 100 that includes a tubular member 108, and has a proximal end 101 and a distal end 102. The tubular member 108 preferably defines a longitudinal length 107 between the proximal and distal ends 101,102, and has a cross dimension or diameter 109 along the length 107. Preferably, the length 107 and diameter 109 are of sufficient size and proportion to allow physician to easily grip the insertion tool 100 with a single hand for manipulation of the insertion tool 100 and the retractor 20 engaged therewith. Preferably the tubular member is hollow, and has an inner cross dimension sufficiently sized to receive a portion of nested tissue dilators therethrough after insertion of the retractor 20 into a dilated incision over the tissue dilators, as will be described in more detail below. A plurality of dilators configured for sequentially dilating tissue within an incision therefore are preferably provided for use with the insertion tool. Preferably, the insertion tool includes at least one viewing port defined therein to allow visual inspection of the dilators therein. As embodied herein, the tubular portion 108 includes a plurality of slots 106 disposed along a portion of the longitudinal length 107 thereof. Upon insertion of the retractor 20 into an incision over dilators using the insertion tool 100, the slots 106 allow a physician to ensure the dilators are received through the tubular member 101, and properly position the members.

A variety of coupling structures can be used in accordance with the invention for example, as embodied in FIG. 15. The coupling structure preferably includes a finger configured to engage a corresponding support structure. Preferably, the finger has an L-shape configured to engage the support structure upon rotation of the insertion tool relative to the retractor. In a preferred embodiment, the finger preferably inhibits movement of the blade at least in one of the first direction, second direction and third direction. More preferably, the finger preferably inhibits movement of the blade in each of the first direction, second direction and third direction. In this manner, the retractor can be positioned with the blades in an unlocked condition, but still inhibit movement of the blade.

As embodied herein, the insertion tool 100 includes an engagement portion 103, such as a hub, that is disposed at the distal end 102 of the insertion tool 100, and preferably configured to engage a portion of the retractor 20. Preferably, the engagement portion includes at least one L-shaped engagement member extending from the hub configured to engage a support structure 50 of the retractor 20. As embodied herein, the engagement portion 103 includes four L-shaped members 104 extending distally therefrom.

The insertion tool 100 is preferably used by engaging the retractor 20 with all four blades in the unretracted position. Prior to insertion of the retractor 20 within the incision, the retractor components (i.e. the frame 30, the blades 40, the support structures 50, and the mounting members 60) are all preferably in unlocked positions and can move relative to each other. Engagement of the retractor 20 by the insertion tool 100, however, acts to stabilize many of the components of the retractor 20 to simplify insertion of the retractor 20 within the incision.

Figure 16B:
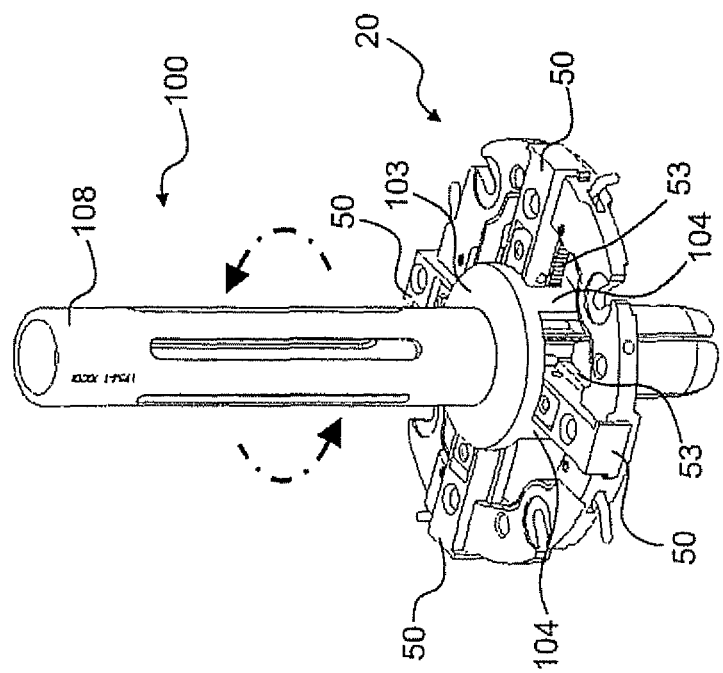
FIG. 16b depicts a perspective view of the retractor assembly of FIG. 16a upon engagement therebetween.
Figure 16A:
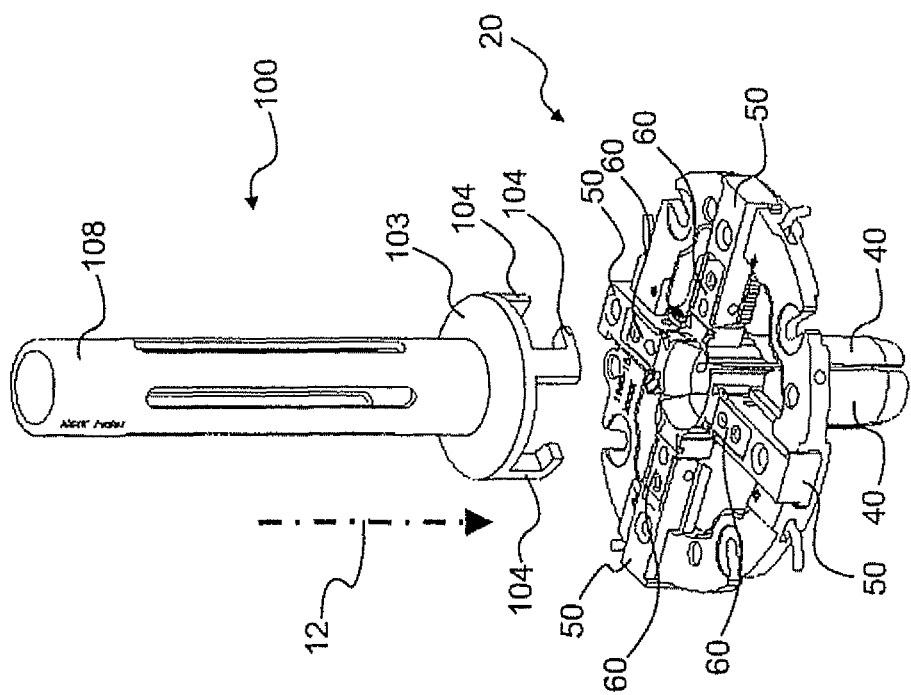
FIG. 16a depicts a perspective view of the insertion tool of FIG. 15 and a retractor prior to engagement therebetween.

Engagement of the retractor 20 is preferably achieved by moving the insertion tool 100 axially such that the engagement portion 103 approaches the proximal ends of the blades 40, as shown in FIG. 16a. Prior to engagement, the insertion tool 100 is preferably rotated such that the L-shaped members 104 are aligned between adjacent mounting members 60. The insertion tool 100 is then moved axially until the engagement portion 103 contacts the proximal ends of the blades 40 and mounting members 60 over the working channel 70.

As shown in FIG. 16b, the insertion tool 100 is then preferably rotated counter-clockwise about a quarter of a revolution such that each of the L-shaped members 104 engages beneath the lateral edge 53 of a respective support structure 50, and behind the respective blade 40. The interlocking engagement between the insertion tool 100 and the retractor 20 allows the physician to easily manipulate and control the position of the retractor 20 during insertion into the incision.

Additionally, the interlocking engagement prevents the retractor components from moving with respect to each other during insertion. For example, each of the support structures 50 is fixed in the unretracted position because abutment of the retraction surface 44 of the blade 40 against the L-shaped portion 104 prevents the support structure 50 from moving in the first direction 10. Similarly, each of the blades 40 is prevented from moving in the second direction 12 due to the abutment of the proximal end 42 of the blade 40 against the engagement portion 103. Finally, each of the blades 40 is prevented from rotating in the third direction 14 due to the abutment of the mounting member 60 against the engagement portion 103.

With the insertion tool 100 and the retractor 20 in interlocking engagement, the retractor 20 can be inserted within the incision that has been previously dilated, for example, with a plurality of nested dilators as shown in FIG. 17a. As embodied herein, a series of nested dilators 110 are used to initially dilate skin and tissue away from a target site on a portion of the spine 112, as shown in FIG. 17a. A K-wire can be used for placement of the dilators if desired. The insertion tool 100 is then used to insert the retractor 20 in the incision over one or more dilator(s) 110, as shown in FIG. 17b. Upon insertion, the dilators 110 are received through the working channel 70 defined by the blades 40, and the tubular member 101, such that the retractor 20 can be fully inserted within the incision. Advantageously, the slots 106 of the insertion tool 100 allow the physician to see the movement of the retractor/insertion tool assembly relative to the dilator(s). This allows the physician to ensure that the insertion tool 100 is moving the retractor 20 within the incision relative to the dilator(s) 110, rather than accidentally moving both the retractor 20 and the dilator(s) 110 further into the incision. Once the retractor 20 is fully inserted within the incision, the insertion tool 100 can be removed, as shown in FIG. 17c. Preferably, the insertion tool 100 is rotated clockwise about a quarter of a revolution such that each of the L-shaped members 104 disengage from beneath the lateral edge 53 of the respective support structures 50, and from the corresponding blade 40. The insertion tool 100 can then be removed from the dilator (s) 112. Finally, as shown in FIG. 17d, the dilators 112 are removed from within the working channel 70 of the retractor 20, with the target site exposed and unobstructed view through the working channel 70.

Figure 8:
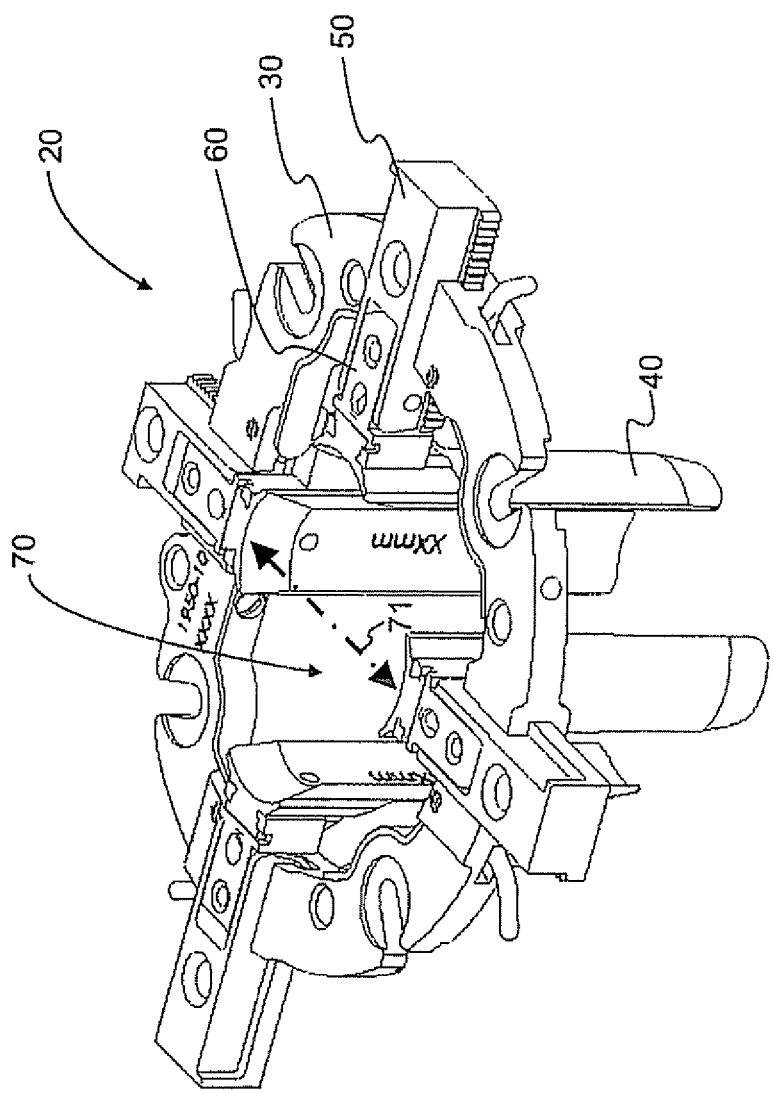
FIG. 8 depicts a perspective view of a representative embodiment of a retractor with four blades in the retracted position.
Figure 9:
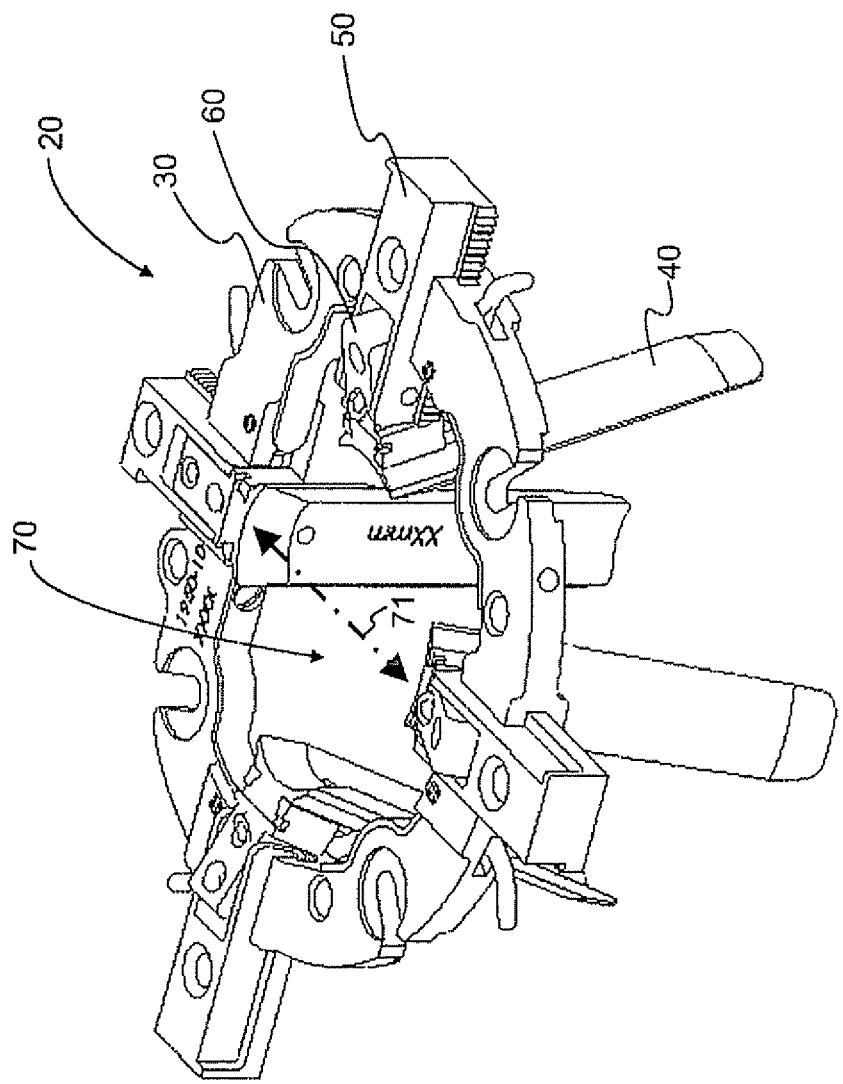
FIG. 9 depicts a perspective view of the retractor of FIG. 8 with the four blades each in the retracted and angled position.

After insertion and placement of the retractor 20 within the incision, the retractor 20 can be adjusted to enlarge the working channel 70 such that skin and tissue is retracted away from the surgical site as desired, as shown in FIGS. 8 and 9. For example, the worm gear 62 can be adjusted either by application of sufficient force on the proximal end portion of the blade or with the leverage tool 63 to move the blade 40 in the second direction 12 adjust the depth of the blades, and thus the working channel, within the incision. Similarly, the support structures 50 can be independently moved in the first direction 10, or the blades 40 can be independently rotated in the third direction 14, to increase the size or diameter 71 of the working channel 70. Movement of the support structure and the rotation of the blades can be achieved by the application of manual force, or with the assistance of a tool in accordance with additional aspects of the invention.

For example, a tool is provided for removable engagement with the retractor to move the blade selectively relative to the reference plane in the first direction. Preferably, the tool includes a first arm removably engageable in a fixed location relative to the blade and a second arm removably engageable for movement with the blade, and the second arm is movable relative to the first arm to move the blade selectively relative the reference plane. Preferably, the first arm is hinged relative the second arm. Also, the first arm and second arm are preferably biased away from each other.

For example, and in accordance with one aspect of the invention as embodied in FIGS. 10, 11a, 11b, 12a, and 12b, the tool is a distractor tool 80 that includes a first arm 81 and a second arm 82. Each arm has a handle portion 83 and an engagement portion 84. As embodied herein for purpose of illustration, the first and second arms 81,82 are in hinged association with each other about hinge member 85. As the handle portions 83 of the first and second arms 81,82 are compressed towards each other to a compressed position, the engagement portions 84 of the arms move away from each other. Similarly, as the handle portions 83 move away from each other, the engagement portions 84 move towards each other. As embodied herein, the handle portions of the distractor tool 80 preferably are biased away from each other, such as by bias members 86 disposed between the handle portions 83 of the first and second arms 81,82 as schematically depicted.

The arms 81,82 of the distractor tool 80 are preferably configured for operation with two hands such that adequate force can be applied to compress the handle portions 83 together. Alternatively, the handle members can be configured for operation with a single hand if desired. Furthermore, alternative configurations that allow relative movement between the engagement portions of the first and second arms can be used.

Figures 12A, 12B:
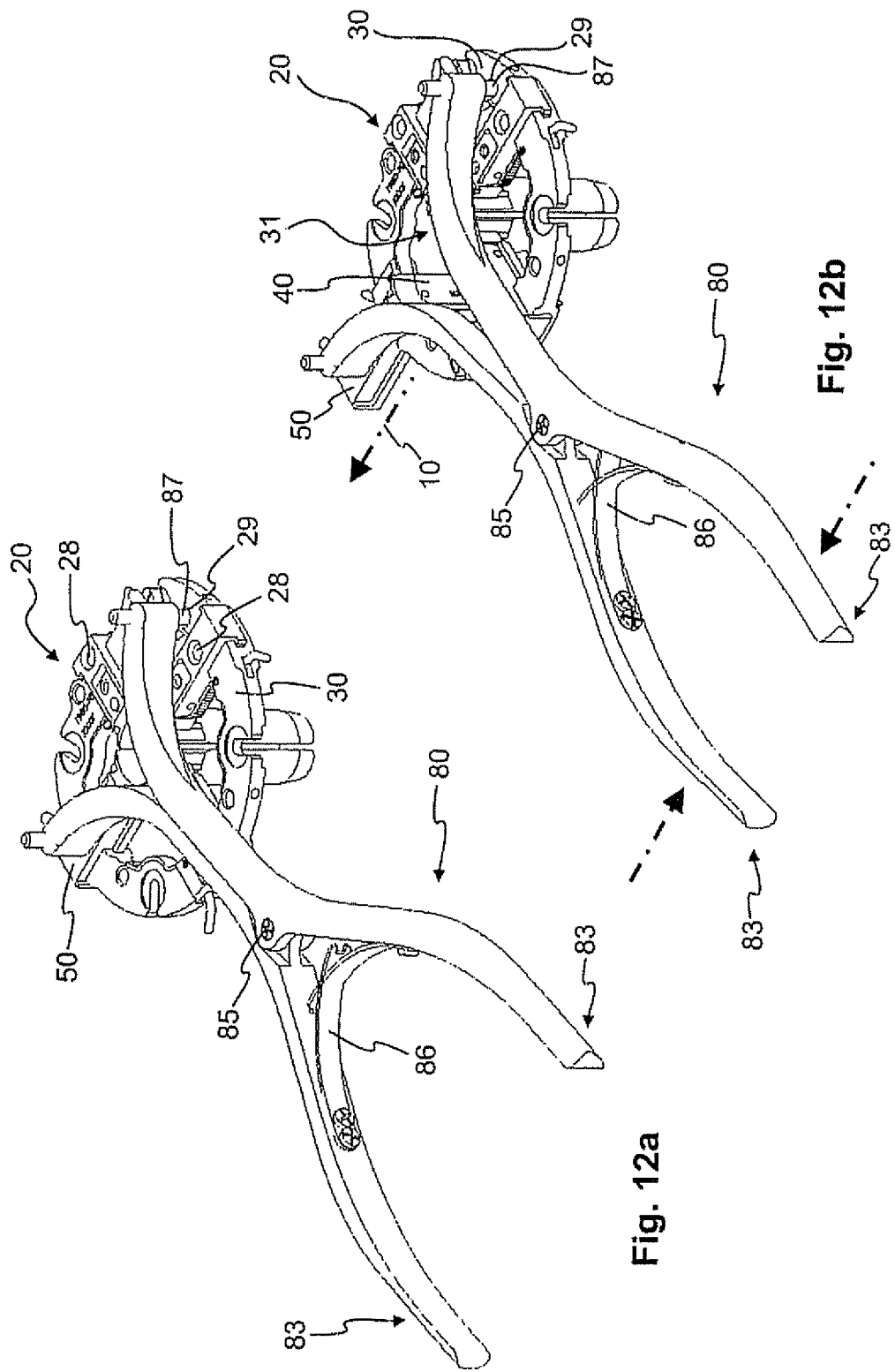
FIG. 12a depicts a perspective view of the distractor tool of FIG. 10 engaged in a second orientation with a frame and support structure of a retractor.
FIG. 12b depicts a perspective view of the retractor assembly of FIG. 12a with the handles of the distractor tool moved toward the compressed position to distract the corresponding blade.

In one preferred embodiment, the tool includes a first engagement portion on the first arm and a second engagement portion on the second arm, wherein the first engagement portion engageable with the frame. For example, as embodied herein, the distractor tool 80 preferably includes first and second engagement protrusions 87,88 disposed at the ends of the engagement portions 84 of the first and second arms 81,82. The engagement protrusions 87,88 are configured for receipt within a recess 29 on the surface of the frame 30 and a recess 28 on the body 56 of a support structure 50, respectively. In one embodiment, the engagement protrusions are disposed on the distal surfaces of the first and second arms, adjacent the engagement portions, to facilitate a vertical engagement of the distractor tool with the retractor as shown in FIG. 11a. Additionally, or alternatively, the engagement protrusions are disposed on the lateral surfaces of the first and second arms, adjacent the engagement portions, to facilitate a horizontal engagement of the distractor tool with the retractor as shown in FIG. 12a. As embodied herein, the distractor tool 80 preferably includes engagement protrusions 87,88 on both the distal and lateral surfaces of the arms 81,82, adjacent the engagement portions 84, such that the distractor tool 80 can be used for both vertical and horizontal engagement.

The distractor tool 80 is preferably used by engaging the retractor 20 to move independently a single support structure 50 in the first direction 10 after the retractor 20 is initially inserted within an incision. As shown in FIG. 11a, for example, the retractor 20 is inserted within the incision with the blades and corresponding support structures 50 in the unretracted positions over the target site. The distractor tool 80 can vertically engage the retractor 20 by inserting the first engagement protrusion 87 of the first arm 81 within the recess 28 of the desired support structure 50, and inserting the second engagement protrusion 88 of the second arm 82 within a recess 29 on the portion of the frame 30 generally opposing (and slightly offset from) the support structure 50. Once the distractor tool 80 is engaged with both the frame 30 and the support structure 50, the handle portions 83 of the first and second arms 81,82 are compressed towards each other to the compressed position, as shown in FIG. 11b. This movement in turn acts to separate the engagement portions 84, and as a result, moves the support structure 50 and corresponding blade 40 in the first direction 10 away from the central opening 31, and into a retracted position to retract skin and tissue away from the target site. Once the support structure 50 is moved to a desired retraction position in the first direction 10, the locking mechanism 34 can manually or automatically be activated or adjusted to the locked position to lock the support structure 50 in the selected retraction position. Similarly, upon unlocking of the locking member 34, the handle portions 83 can be moved away from each other to move the engagement portions 84 towards each other, which acts to move the support structure 50 and corresponding blade 40 in the first direction 10 toward the unretracted position. After moving the support structure 50 to a desired position, the distractor tool 80 can be disengaged from the support structure and the frame, and then engaged with another support structure 50 for similar movement thereof, if desired.

The distractor tool 80 can also engage the retractor 20 from a horizontal approach. As shown in FIG. 12a, for example, the first engagement protrusion 87 on the lateral surface of the first arm 81 is inserted within the recess 28 of a support structure 50, and the second engagement protrusion 88 on the lateral surface of the second arm 82 is inserted within the recess 29 on the portion of the frame 30 opposing and slightly offset from the support structure 50. Once engaged, the distractor tool 80 can be operated as described above to move the support structure 50 in the first direction 10 and corresponding blade 40, as shown in FIG. 12b. Engagement of the distractor tool 80 with the retractor 20 in either the vertical or horizontal approach provides similar distraction forces to the support structures 50, and selection of one approach over the other is dependent on the presence of obstructions in and around the working channel 70, and access thereto, and personal preference.

Figure 13:
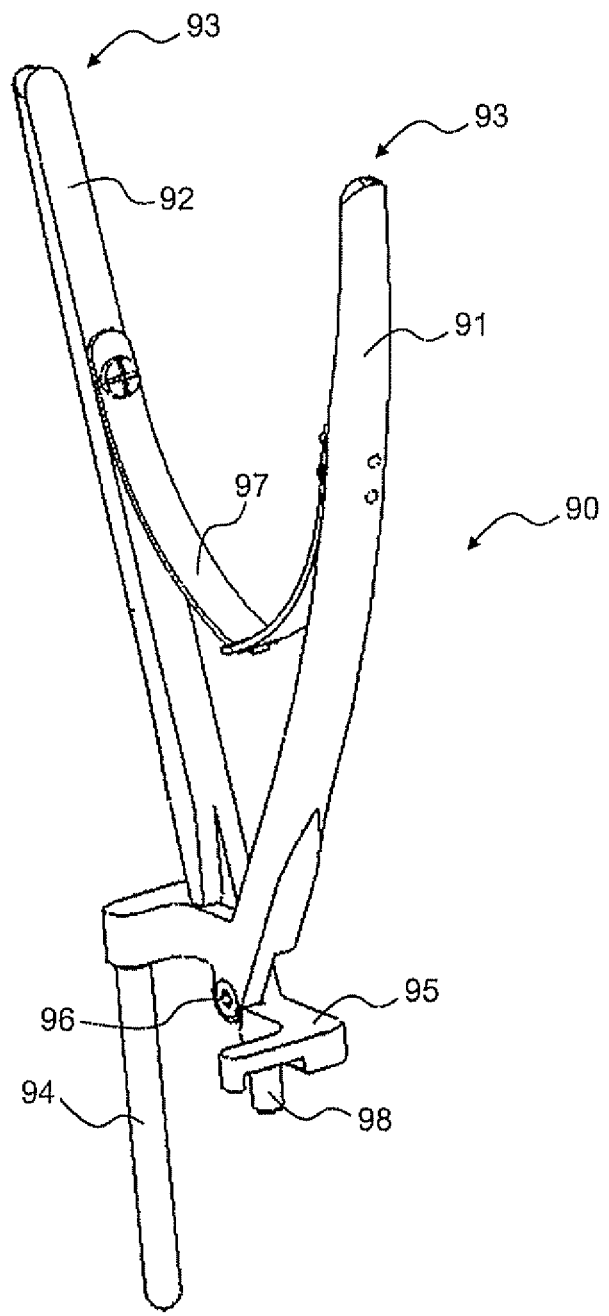
FIG. 13 depicts a perspective view of a representative embodiment of a pivot tool in accordance with another aspect of the invention.

In accordance with another aspect of the invention, a tool is provided to remove engagements with the retractor to pivot a blade relative to its corresponding support structure in the third direction. For example, and as embodied in FIG. 13, a pivot tool 90 is provided that includes first and second arms 91,92, each arm further including a handle portion 93. Disposed at the end of the first arm 91 opposite the handle portion 93 is a blade engagement portion 94, and disposed at the end of the end of the second arm 92 opposite the handle portion 93 is a support structure engagement portion 95.

The first and second arms 91,92, as embodied herein for purpose of illustration, are in hinged association with each other about hinge member 96. As the handle portions 93 of the first and second arms 91,92 are compressed towards each other to a compressed position, the blade engagement portion 94 rotates about the hinge member 96 and away from the support structure engagement portion 95. Similarly, as the handle portions 93 are brought away from each other, the blade engagement portions 94 rotates toward the support structure engagement portion 95. As embodied herein and schematically depicted, the pivot tool 90 preferably includes a bias member 97 disposed between the handle portions 93 of the first and second arms 91,92. The bias member 97 acts to bias the handle portions 93 away from each other toward an uncompressed position.

The arms 91,92 of the pivot tool 90 are preferably configured for operation with two hands such that adequate force can be applied to compress the handle portions 93 together. In some embodiments, the handle members can be configured for operation with a single hand such that a physician's other hand is free to operate another surgical instrument.

As embodied herein, blade engagement portion 94 has an extended configuration to associate with the inward-facing surface 43 of a blade 40 along the length of the blade 46. The support structure engagement portion 95 preferably includes a protrusion 98 that is configured for receipt within the recess 28 on the body 56 of a support structure 50.

The pivot tool 90 is preferably used by engaging the retractor 20 to rotate a single blade 40 independently in the third direction 14 after the retractor 20 is initially inserted within an incision. Beneficially, the blade 40 can be rotated with the pivot tool 90 before or after movement of the support structure 50 to a retracted position in the first direction 10, as described above.

As shown in FIG. 14a, for example, the retractor 20 is inserted within the incision with the support structures 50 and corresponding blade 40 in the unretracted positions over the target site, and with all blades 40 disposed substantially orthogonal to the reference plane 32. The pivot tool 90 embodied herein can engage the retractor 20 by inserting the protrusion of the support structure engagement portion 95 within the recess 28 of a support structure 50, and engaging the blade engagement portion 94 along the inward-facing surface 43 of the blade 40 that is associated with the support structure 50. Once the pivot tool 90 is engaged with both the support structure 50 and the blade 40, the handle portions 93 of the first and second arms 91,92 are compressed towards each other to the compressed position, as shown in FIG. 14b. This movement in turn acts to rotate the blade engagement portion 94 and thus the blade toward the support structure upon which the blade is supported. That is, the blade 40 rotates in the third direction 14 to a retraction angle to retract skin and tissue away from the target site. Once the blade 40 is rotated to a desired retraction angle in the third direction 14, the locking mechanism 64 can be adjusted to the locked position to lock the blade in the selected retraction angle. After rotating the blade 40 to a desired angle, the pivot tool 90 can be disengaged from the support structure and the blade, and then engaged with another blade 40 for similar movement thereof. If desired, the blade engagement portion can be configured to couple with the blade such that upon unlocking of the locking member 64, the handle portions 93 can be moved away from each other to rotate the blade engagement portions 94 away from the support structure and rotate the blade 40 in the third direction 12 toward the unretracted position. Alternatively, the retracted tissue can act to return the blade to the unretracted position upon unlocking the locking mechanism.

Figure 18:
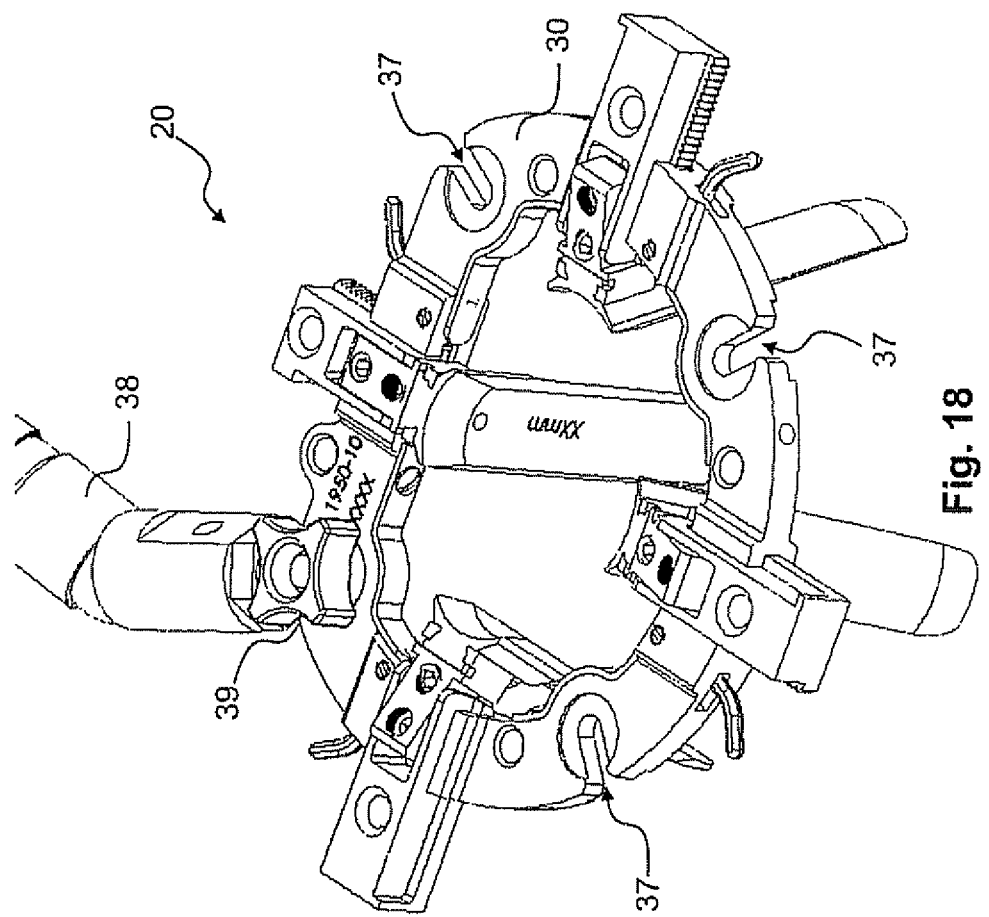
FIG. 18 depicts a perspective view of an embodiment of a retractor engaged to an articulating snake arm.

The frame of the retractor also can include at least one stabilizing portion disposed on the surface of the frame. Preferably, the stabilizing portion is configured for engagement with a stabilizing member that is stably attached to the operating table or other stationary object to fix the position of the retractor at a certain orientation relative to the operating table and the patient. As embodied in FIG. 18, the frame 30 includes four C-shaped notches 37 disposed about the surface of the frame. The notches 37 are configured to matingly engage the end of a articulating snake arm 38 to stably support the retractor 20 in any number of fixed positions. Preferably, the end of the snake arm 38 also includes a locking mechanism 39, embodied herein as a screw clamp that is configured to secure the frame 30 in mating engagement with the snake arm 38. Other configurations can be used.

In some embodiments, frame also preferably includes an attachment portion to attach surgical instruments or the like thereto. Such instruments can include, for example, light sources, suction tubes, retractors, scissors, and/or imaging devices (e.g., laparoscopes). Preferably, the instruments can be positioned through one or more openings formed in the frame. In some embodiments, the instruments are be clamped, screwed, or otherwise attached to the frame.

The retractor and tools of the present invention can be made of materials that allow the retractor to be heat and/or chemically sterilized. Components of the retractor can be made of metal (including steel and aluminum), ceramics and/or polymers. In some embodiments, the retractor and/or blades can be formed of a radiolucent material. The radiolucent material advantageously allows radiological imaging of a surgical site while the retractor is in use. Preferably, the radiolucent material is a polymer or a carbon-reinforced polymer. More preferably, the polymer can be polyetheretherketone (PEEK). In some embodiments, radio-opaque markers can be placed at selected locations of the retractor. For example, a tantalum bead or member can be positioned at or near the distal end of a blade so that the position of the blade is indicated in radiological images taken during a surgical procedure. Radio-opaque markers can also be positioned on the frame and/or along one or more of the blade surfaces. Preferably, a portion of a blade is formed of a polymeric material includes radio-opaque material (e.g., barium doping) so that a position of the blade is indicated on radiological images taken during a surgical procedure.

The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments can be devised by those of ordinary skill in the art. Features of the embodiments described herein can be combined, separated, interchanged, and/or rearranged to generate other embodiments. Therefore, it will be understood that the appended claims are intended to cover all such modifications and embodiments that come within the spirit and scope of the present invention.

What is claimed is:

1. A retractor for insertion in an incision of a patient, the retractor comprising:
a frame defining a central opening and a reference plane, the frame having an upper surface and an opposing lower surface, the frame configured such that the lower surface faces the patient and the upper surface faces away from the patient during use;
at least one blade disposed within the central opening, the blade operatively coupled to the frame by a support structure that provides sliding movement in a first direction generally laterally with the reference plane, the support structure providing sliding movement of the blade in a second direction rotationally relative to the reference plane;
a first adjustment mechanism configured to slide the blade in the first direction;
a second adjustment mechanism configured to slide the blade in the second direction, wherein the first and second adjustment mechanisms are both accessed and actuated from the upper surface of the frame;
a locking mechanism to prevent rotational movement of the blade relative the support structure; and
the frame including a track in mating relationship with the support structure for sliding movement therebetween in a defined relationship relative to the reference plane.

2. The retractor of claim 1, wherein the support structure includes a lateral edge with a dovetail configuration in mating relation with the track.

3. The retractor of claim 1, further comprising a locking mechanism to prevent sliding movement of the support structure relative to the frame when in a locked position.

4. The retractor of claim 3, wherein the support structure includes a lateral edge with a plurality of teeth defined therein, the locking mechanism configured to engage at least one of the plurality of teeth when in the locked position.

5. The retractor of claim 1, wherein the blade is pivotally mounted on the support structure by a mounting member for rotational movement in the second direction.

6. The retractor of claim 5, wherein the mounting member is pivotally connected to the support structure.

7. The retractor of claim 1, comprising a plurality of blades disposed within the central opening, each blade operatively coupled to the frame by a corresponding support structure for movement in the first direction and the second direction, respectively;
each blade including an inwardly-facing surface and a pair of lateral edges, each inwardly-facing surface defining a portion of a working channel formed when the blades are in an unretracted position with the lateral edges of adjacent blades disposed proximate each other.

8. The retractor of claim 7, wherein the working channel has a central axis defined therethrough; each blade capable of being moved from the unretracted position in the first direction away from the central axis and having a distal end capable of being rotated in the second direction away from the central axis.

9. A retractor for insertion in an incision of a patient, the retractor comprising:
a frame defining a central opening and a reference plane, the frame defining a central axis extending through the central opening substantially perpendicular to the reference plane, the frame having an upper surface and an opposing lower surface, the frame configured such that the lower surface faces the patient and the upper surface faces away from the patient during use;
a first blade disposed within the central opening, the first blade operatively coupled to the frame by a first support structure that provides lateral movement relative to the reference plane, the first blade having a distal end portion and a proximal end portion, the proximal end portion of the first blade coupled with the first support structure, the first support structure providing pivoting movement of the first blade rotationally relative to the reference plane to adjust an angle of the first blade within the incision relative to the central axis;

a second blade disposed within the central opening, the second blade operatively coupled to the frame by a second support structure that provides lateral movement relative to the reference plane, the second blade having a distal end portion and a proximal end portion, the proximal end portion of the second blade coupled with the second support structure, the second support structure providing pivoting movement of the second blade rotationally relative to the reference plane to adjust an angle of the second blade within the incision relative to the central axis;

first and second adjustment mechanisms configured to slide the first and second blades laterally relative to the reference plane, respectively;

third and fourth adjustment mechanisms configured to pivot the first and second blades rotationally relative to the central axis, wherein the first, second, third, and fourth adjustment mechanisms are all accessed and actuated from the upper surface of the frame; and wherein the first blade moves laterally and rotationally independently from the second blade.

10. The retractor of claim 9, wherein the first support structure includes a lateral edge with a dovetail configuration in mating relation with a track on the frame.

11. The retractor of claim 9, further comprising a locking mechanism to prevent sliding movement of the first support structure laterally relative to the frame when in a locked position.

12. The retractor of claim 11, wherein the first support structure includes a lateral edge with a plurality of teeth defined therein, the locking mechanism configured to engage at least one of the plurality of teeth when in the locked position.

13. The retractor of claim 9, further comprising first and second locking mechanisms to prevent rotational movement of the first and second blades relative the first and second support structures, respectively.

14. The retractor of claim 13, wherein the first and second locking mechanisms are screws.

* * * * *